United States Patent
Hsu et al.

(10) Patent No.: US 11,524,045 B2
(45) Date of Patent: Dec. 13, 2022

(54) PEPTIDES FOR DRY EYE DISEASE

(71) Applicant: ALLYSTA PHARMACEUTICALS, INC., Belmont, CA (US)

(72) Inventors: Henry Hsu, Belmont, CA (US); Laszlo Otvos, Audubon, PA (US)

(73) Assignee: ALLYSTA PHARMACEUTICALS, INC., Bellevue, WA (US)

( * ) Notice: Subject to any disclaimer, the term of this patent is extended or adjusted under 35 U.S.C. 154(b) by 375 days.

(21) Appl. No.: 16/492,325

(22) PCT Filed: Mar. 6, 2018

(86) PCT No.: PCT/US2018/021232
§ 371 (c)(1),
(2) Date: Sep. 9, 2019

(87) PCT Pub. No.: WO2018/165218
PCT Pub. Date: Sep. 13, 2018

(65) Prior Publication Data
US 2021/0128677 A1   May 6, 2021

Related U.S. Application Data

(60) Provisional application No. 62/469,170, filed on Mar. 9, 2017.

(51) Int. Cl.
| | | |
|---|---|---|
| A61K 38/10 | (2006.01) | |
| A61P 27/02 | (2006.01) | |
| A61K 9/00 | (2006.01) | |
| A61K 31/4725 | (2006.01) | |
| A61K 45/06 | (2006.01) | |
| A61P 27/04 | (2006.01) | |
| C07K 7/02 | (2006.01) | |
| C07K 7/06 | (2006.01) | |

(52) U.S. Cl.
CPC ............ *A61K 38/10* (2013.01); *A61K 9/0048* (2013.01); *A61K 31/4725* (2013.01); *A61K 45/06* (2013.01); *A61P 27/02* (2018.01); *A61P 27/04* (2018.01); *C07K 7/02* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 2015/0051137 A1* | 2/2015 | Rainger | A61P 9/00 514/7.3 |
| 2016/0152704 A1 | 6/2016 | Chimen et al. | |
| 2017/0151309 A1* | 6/2017 | Rainger | A61K 38/1709 |

FOREIGN PATENT DOCUMENTS

| | | |
|---|---|---|
| WO | 2011159661 A1 | 12/2011 |
| WO | 2016179007 A1 | 11/2016 |
| WO | 2017006272 A1 | 1/2017 |

OTHER PUBLICATIONS

Nuijens et al. "Enzymatic C-terminal amidation of amino acids and peptides" Tetrahedron Letters 53:3777-3779. (Year: 2012).*
"Sjogren's Syndrome" MedlinePlus https://medlineplus.gov/sjogrenssyndrome.html. (Year: 2016).*
Sheppard et al. "Lifitegrast Ophthalmic Solution 5.0% for Treatment of Dry Eye Disease" Ophthalmology 121:475-483. (Year: 2014).*
Kaplan, A et al. Cellular Signaling, vol. 31, pp. 26-30, 2018.
Li, Z. et al. Investigative Opthalmology and Visual Science, vol. 54, No. 1, pp. 155-162, 2013.
European extended search report on EP18764841, dated Nov. 5, 2020.
Chimen, M et al. Nat. Med. 21(5), 467-475, 2015.
Ozaki, A et al. Micriobiol. Immunol. 48(1), 39-48, 2004.
Schaumburg, C. et al. J. Immunol. 187, 3653-3662, 2011.
International Search Report on PCT/US2018/21232, dated May 25, 2018.

* cited by examiner

*Primary Examiner* — Sudhakar Katakam
*Assistant Examiner* — Zachary J Miknis
(74) *Attorney, Agent, or Firm* — Lin Sun-Hoffman; Yong Chen; Liu Chen & Hoffman LLP

(57) ABSTRACT

Disclosed are ophthalmic compositions, methods for using the compositions and kits comprising the compositions for treating dry eye in a subject in need thereof. The composition comprises at least one peptide that is an inhibitor of trans-endothelial migration, an analogue, variant, derivative, or a pharmaceutically acceptable salt thereof, and a pharmaceutically acceptable excipient for treating dry eye and ocular diseases of inflammation.

13 Claims, 4 Drawing Sheets

Specification includes a Sequence Listing.

\* P< 0.05 vs. Dry Eye Vehicle

\* P< 0.05 vs. Dry Eye Vehicle

Severe,
Grade 4

Corneal staining assessed in 4 quadrants using 4-point scale
(max score: 16)

18.86%

32.86%

26.73%

21.67%

SEQUENCE LISTING

```
<160> NUMBER OF SEQ ID NOS: 35

<210> SEQ ID NO 1
<211> LENGTH: 14
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
```

```
<222> LOCATION: (14)..(14)
<223> OTHER INFORMATION: The C-terminal amino acid at position 14 is
      optionally amidated

<400> SEQUENCE: 1

Ser Val Thr Glu Gln Gly Ala Glu Leu Ser Asn Glu Glu Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-form Serine
<220> FEATURE:
<221> NAME/KEY: MISC_FEATURE
<222> LOCATION: (3)..(3)
<223> OTHER INFORMATION: Xaa at position 3 is Allo-threonine
<220> FEATURE:
<221> NAME/KEY: MISC_FEATURE
<222> LOCATION: (9)..(9)
<223> OTHER INFORMATION: Xaa at position 9 is norleucine
<220> FEATURE:
<221> NAME/KEY: MISC_FEATURE
<222> LOCATION: (12)..(12)
<223> OTHER INFORMATION: Xaa at position 12 is N-Methyl-Glu
<220> FEATURE:
<221> NAME/KEY: MOD_RES
<222> LOCATION: (14)..(14)
<223> OTHER INFORMATION: The C-terminal amino acid at position 14 is
      optionally amidated
<220> FEATURE:
<221> NAME/KEY: MISC_FEATURE
<222> LOCATION: (14)..(14)
<223> OTHER INFORMATION: Xaa at position 14 is ornithine

<400> SEQUENCE: 2

Xaa Val Xaa Glu Gln Gly Ala Glu Xaa Ser Asn Xaa Glu Xaa
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is hydroxyproline
<220> FEATURE:
<221> NAME/KEY: MISC_FEATURE
<222> LOCATION: (4)..(4)
<223> OTHER INFORMATION: Xaa at position 4 is N-methyl-glutamic acid
<220> FEATURE:
<221> NAME/KEY: MISC_FEATURE
<222> LOCATION: (10)..(10)
<223> OTHER INFORMATION: Xaa at position 10 is hydroxyproline
<220> FEATURE:
<221> NAME/KEY: MISC_FEATURE
<222> LOCATION: (11)..(11)
<223> OTHER INFORMATION: Xaa at position 11 is D-asparagine
<220> FEATURE:
<221> NAME/KEY: MOD_RES
<222> LOCATION: (14)..(14)
<223> OTHER INFORMATION: The C-terminal amino acid at position 14 is
      optionally amidated
<220> FEATURE:
<221> NAME/KEY: MISC_FEATURE
<222> LOCATION: (14)..(14)
<223> OTHER INFORMATION: Xaa at position 14 is 6-amino-hexanoic acid
```

```
<400> SEQUENCE: 3

Xaa Val Thr Xaa Gln Gly Ala Glu Leu Xaa Xaa Glu Glu Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (13)..(13)
<223> OTHER INFORMATION: The C-terminal amino acid at position 13 is
      optionally amidated

<400> SEQUENCE: 4

Ser Val Thr Glu Gln Gly Ala Glu Leu Ser Asn Glu Glu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-serine
<220> FEATURE:
<221> NAME/KEY: MISC_FEATURE
<222> LOCATION: (3)..(3)
<223> OTHER INFORMATION: Xaa at position 3 is Allo-threonine
<220> FEATURE:
<221> NAME/KEY: MISC_FEATURE
<222> LOCATION: (9)..(9)
<223> OTHER INFORMATION: Xaa at position 9 is norleucine
<220> FEATURE:
<221> NAME/KEY: MISC_FEATURE
<222> LOCATION: (12)..(12)
<223> OTHER INFORMATION: Xaa at position 12 is N-methyl-glutamic acid
<220> FEATURE:
<221> NAME/KEY: MOD_RES
<222> LOCATION: (13)..(13)
<223> OTHER INFORMATION: The C-terminal amino acid at position 13 is
      optionally amidated
<220> FEATURE:
<221> NAME/KEY: MISC_FEATURE
<222> LOCATION: (13)..(13)
<223> OTHER INFORMATION: Xaa at position 13 is glutamic acid methyl
      ester

<400> SEQUENCE: 5

Xaa Val Xaa Glu Gln Gly Ala Glu Xaa Ser Asn Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (13)..(13)
<223> OTHER INFORMATION: The C-terminal amino acid at position 13 is
      optionally amidated

<400> SEQUENCE: 6

Val Thr Glu Gln Gly Ala Glu Leu Ser Asn Glu Glu Arg
```

```
1               5                   10
```

<210> SEQ ID NO 7
<211> LENGTH: 13
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is norvaline
<220> FEATURE:
<221> NAME/KEY: MISC_FEATURE
<222> LOCATION: (2)..(2)
<223> OTHER INFORMATION: Xaa at position 2 is Allo-threonine
<220> FEATURE:
<221> NAME/KEY: MISC_FEATURE
<222> LOCATION: (8)..(8)
<223> OTHER INFORMATION: Xaa at position 8 is norleucine
<220> FEATURE:
<221> NAME/KEY: MISC_FEATURE
<222> LOCATION: (11)..(11)
<223> OTHER INFORMATION: Xaa at position 11 is N-methyl-glutamic acid
<220> FEATURE:
<221> NAME/KEY: MOD_RES
<222> LOCATION: (13)..(13)
<223> OTHER INFORMATION: The C-terminal amino acid at position 13 is
      optionally amidated
<220> FEATURE:
<221> NAME/KEY: MISC_FEATURE
<222> LOCATION: (13)..(13)
<223> OTHER INFORMATION: Xaa at position 13 is ornithine

<400> SEQUENCE: 7

Xaa Xaa Glu Gln Gly Ala Glu Xaa Ser Asn Xaa Glu Xaa
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (12)..(12)
<223> OTHER INFORMATION: The C-terminal amino acid at position 12 is
      optionally amidated

<400> SEQUENCE: 8

Val Thr Glu Gln Gly Ala Glu Leu Ser Asn Glu Glu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is norvaline
<220> FEATURE:
<221> NAME/KEY: MISC_FEATURE
<222> LOCATION: (2)..(2)
<223> OTHER INFORMATION: Xaa at position 2 is Allo-threonine
<220> FEATURE:
<221> NAME/KEY: MISC_FEATURE
<222> LOCATION: (8)..(8)
<223> OTHER INFORMATION: Xaa at position 8 is norleucine
<220> FEATURE:
<221> NAME/KEY: MISC_FEATURE

```
<222> LOCATION: (11)..(11)
<223> OTHER INFORMATION: Xaa at position 11 is N-methyl-glutamic acid
<220> FEATURE:
<221> NAME/KEY: MOD_RES
<222> LOCATION: (12)..(12)
<223> OTHER INFORMATION: The C-terminal amino acid at position 12 is
      optionally amidated
<220> FEATURE:
<221> NAME/KEY: MISC_FEATURE
<222> LOCATION: (12)..(12)
<223> OTHER INFORMATION: Xaa at position 12 is glutamic acid methyl
      ester

<400> SEQUENCE: 9

Xaa Xaa Glu Gln Gly Ala Glu Xaa Ser Asn Xaa Xaa
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is 1-amino-cyclohexyl
      carboxylic acid
<220> FEATURE:
<221> NAME/KEY: MISC_FEATURE
<222> LOCATION: (3)..(3)
<223> OTHER INFORMATION: Xaa at position 3 is N-methyl-glutamic acid
<220> FEATURE:
<221> NAME/KEY: MISC_FEATURE
<222> LOCATION: (9)..(9)
<223> OTHER INFORMATION: Xaa at position 9 is hydroxyproline
<220> FEATURE:
<221> NAME/KEY: MISC_FEATURE
<222> LOCATION: (10)..(10)
<223> OTHER INFORMATION: Xaa at position 10 is D-asparagine
<220> FEATURE:
<221> NAME/KEY: MOD_RES
<222> LOCATION: (12)..(12)
<223> OTHER INFORMATION: The C-terminal amino acid at position 12 is
      optionally amidated
<220> FEATURE:
<221> NAME/KEY: MISC_FEATURE
<222> LOCATION: (12)..(12)
<223> OTHER INFORMATION: Xaa at position 12 is D-glutamine

<400> SEQUENCE: 10

Xaa Thr Xaa Gln Gly Ala Glu Leu Xaa Xaa Glu Xaa
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (11)..(11)
<223> OTHER INFORMATION: The C-terminal amino acid at position 11 is
      optionally amidated

<400> SEQUENCE: 11

Val Thr Glu Gln Gly Ala Glu Leu Ser Asn Glu
1               5                   10

<210> SEQ ID NO 12
<211> LENGTH: 11
<212> TYPE: PRT
```

```
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is norvaline
<220> FEATURE:
<221> NAME/KEY: MISC_FEATURE
<222> LOCATION: (2)..(2)
<223> OTHER INFORMATION: Xaa at position 2 is Allo-threonine
<220> FEATURE:
<221> NAME/KEY: MISC_FEATURE
<222> LOCATION: (8)..(8)
<223> OTHER INFORMATION: Xaa at position 8 is norleucine
<220> FEATURE:
<221> NAME/KEY: MOD_RES
<222> LOCATION: (11)..(11)
<223> OTHER INFORMATION: The C-terminal amino acid at position 11 is
      optionally amidated
<220> FEATURE:
<221> NAME/KEY: MISC_FEATURE
<222> LOCATION: (11)..(11)
<223> OTHER INFORMATION: Xaa at position 11 is N-methyl-glutamic acid

<400> SEQUENCE: 12

Xaa Xaa Glu Gln Gly Ala Glu Xaa Ser Asn Xaa
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (11)..(11)
<223> OTHER INFORMATION: The C-terminal amino acid at position 11 is
      optionally amidated

<400> SEQUENCE: 13

Thr Glu Gln Gly Ala Glu Leu Ser Asn Glu Glu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is Allo-threonine
<220> FEATURE:
<221> NAME/KEY: MISC_FEATURE
<222> LOCATION: (7)..(7)
<223> OTHER INFORMATION: Xaa at position 7 is norleucine
<220> FEATURE:
<221> NAME/KEY: MISC_FEATURE
<222> LOCATION: (10)..(10)
<223> OTHER INFORMATION: Xaa at position 10 is N-methyl-glutamic acid
<220> FEATURE:
<221> NAME/KEY: MOD_RES
<222> LOCATION: (11)..(11)
<223> OTHER INFORMATION: The C-terminal amino acid at position 11 is
      optionally amidated
<220> FEATURE:
<221> NAME/KEY: MISC_FEATURE
<222> LOCATION: (11)..(11)
<223> OTHER INFORMATION: Xaa at position 11 is glutamic acid methyl
      ester

<400> SEQUENCE: 14
```

```
Xaa Glu Gln Gly Ala Glu Xaa Ser Asn Xaa Xaa
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (10)..(10)
<223> OTHER INFORMATION: The C-terminal amino acid at position 10 is
      optionally amidated

<400> SEQUENCE: 15

```
Thr Glu Gln Gly Ala Glu Leu Ser Asn Glu
1               5                   10
```

<210> SEQ ID NO 16
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is  Allo-threonine
<220> FEATURE:
<221> NAME/KEY: MISC_FEATURE
<222> LOCATION: (4)..(4)
<223> OTHER INFORMATION: Xaa at position 4 is norvaline
<220> FEATURE:
<221> NAME/KEY: MISC_FEATURE
<222> LOCATION: (7)..(7)
<223> OTHER INFORMATION: Xaa at position 7 is norleucine
<220> FEATURE:
<221> NAME/KEY: MOD_RES
<222> LOCATION: (10)..(10)
<223> OTHER INFORMATION: The C-terminal amino acid at position 10 is
      optionally amidated
<220> FEATURE:
<221> NAME/KEY: MISC_FEATURE
<222> LOCATION: (10)..(10)
<223> OTHER INFORMATION: Xaa at position 10 is N-methyl-glutamic acid

<400> SEQUENCE: 16

```
Xaa Glu Gln Xaa Ala Glu Xaa Ser Asn Xaa
1               5                   10
```

<210> SEQ ID NO 17
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-serine
<220> FEATURE:
<221> NAME/KEY: MISC_FEATURE
<222> LOCATION: (8)..(8)
<223> OTHER INFORMATION: Xaa at position 8 is D-serine
<220> FEATURE:
<221> NAME/KEY: MISC_FEATURE
<222> LOCATION: (9)..(9)
<223> OTHER INFORMATION: Xaa at position 9 is D-asparagine
<220> FEATURE:
<221> NAME/KEY: MOD_RES
<222> LOCATION: (10)..(10)
<223> OTHER INFORMATION: The C-terminal amino acid at position 10 is

```
        optionally amidated
<220> FEATURE:
<221> NAME/KEY: MISC_FEATURE
<222> LOCATION: (10)..(10)
<223> OTHER INFORMATION: Xaa at position 10 is D-glutamine

<400> SEQUENCE: 17

Xaa Glu Gln Gly Ala Glu Leu Xaa Xaa Xaa
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (9)..(9)
<223> OTHER INFORMATION: The C-terminal amino acid at position 9 is
        optionally amidated

<400> SEQUENCE: 18

Ser Val Thr Glu Gln Gly Ala Glu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-serine
<220> FEATURE:
<221> NAME/KEY: MISC_FEATURE
<222> LOCATION: (6)..(6)
<223> OTHER INFORMATION: Xaa at position 6 is norvaline
<220> FEATURE:
<221> NAME/KEY: MOD_RES
<222> LOCATION: (9)..(9)
<223> OTHER INFORMATION: The C-terminal amino acid at position 9 is
        optionally amidated
<220> FEATURE:
<221> NAME/KEY: MISC_FEATURE
<222> LOCATION: (9)..(9)
<223> OTHER INFORMATION: Xaa at position 9 is norleucine

<400> SEQUENCE: 19

Xaa Val Thr Glu Gln Xaa Ala Glu Xaa
1               5

<210> SEQ ID NO 20
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is hydroxyproline
<220> FEATURE:
<221> NAME/KEY: MISC_FEATURE
<222> LOCATION: (7)..(7)
<223> OTHER INFORMATION: Xaa at position 7 is beta-alanine
<220> FEATURE:
<221> NAME/KEY: MOD_RES
<222> LOCATION: (9)..(9)
<223> OTHER INFORMATION: The C-terminal amino acid at position 9 is
        optionally amidated
```

```
<220> FEATURE:
<221> NAME/KEY: MISC_FEATURE
<222> LOCATION: (9)..(9)
<223> OTHER INFORMATION: Xaa at position 9 is 6-amino-hexanoic acid

<400> SEQUENCE: 20

Xaa Val Thr Glu Gln Gly Xaa Glu Xaa
1               5

<210> SEQ ID NO 21
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (9)..(9)
<223> OTHER INFORMATION: The C-terminal amino acid at position 9 is
      optionally amidated

<400> SEQUENCE: 21

Val Thr Glu Gln Gly Ala Glu Leu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is norvaline
<220> FEATURE:
<221> NAME/KEY: MISC_FEATURE
<222> LOCATION: (5)..(5)
<223> OTHER INFORMATION: Xaa at position 5 is norvaline
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
<222> LOCATION: (9)..(9)
<223> OTHER INFORMATION: Xaa at position 9 is D-serine

<400> SEQUENCE: 22

Xaa Thr Glu Gln Xaa Ala Glu Leu Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is 1-amino-cyclohexyl
      carboxylic acid
<220> FEATURE:
<221> NAME/KEY: MISC_FEATURE
<222> LOCATION: (6)..(6)
<223> OTHER INFORMATION: Xaa at position 6 is beta-alanine
<220> FEATURE:
<221> NAME/KEY: MOD_RES
<222> LOCATION: (9)..(9)
<223> OTHER INFORMATION: The C-terminal amino acid at position 9 is
      optionally amidated
```

```
<220> FEATURE:
<221> NAME/KEY: MISC_FEATURE
<222> LOCATION: (9)..(9)
<223> OTHER INFORMATION: Xaa at position 9 is hydroxyproline

<400> SEQUENCE: 23

Xaa Thr Glu Gln Gly Xaa Glu Leu Xaa
1               5

<210> SEQ ID NO 24
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (9)..(9)
<223> OTHER INFORMATION: The C-terminal amino acid at position 9 is
      optionally amidated

<400> SEQUENCE: 24

Thr Glu Gln Gly Ala Glu Leu Ser Asn
1               5

<210> SEQ ID NO 25
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is Allo-threonine
<220> FEATURE:
<221> NAME/KEY: MISC_FEATURE
<222> LOCATION: (4)..(4)
<223> OTHER INFORMATION: Xaa at position 4 is norvaline
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
<222> LOCATION: (9)..(9)
<223> OTHER INFORMATION: Xaa at position 9 is D-asparagine

<400> SEQUENCE: 25

Xaa Glu Gln Xaa Ala Glu Leu Ser Xaa
1               5

<210> SEQ ID NO 26
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-serine
<220> FEATURE:
<221> NAME/KEY: MISC_FEATURE
<222> LOCATION: (5)..(5)
<223> OTHER INFORMATION: Xaa at position 5 is beta-alanine
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
```

```
<221> NAME/KEY: MISC_FEATURE
<222> LOCATION: (9)..(9)
<223> OTHER INFORMATION: Xaa at position 9 is D-glutamine

<400> SEQUENCE: 26

Xaa Glu Gln Gly Xaa Glu Leu Ser Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (9)..(9)
<223> OTHER INFORMATION: The C-terminal amino acid at position 9 is
      optionally amidated

<400> SEQUENCE: 27

Glu Gln Gly Ala Glu Leu Ser Asn Glu
1               5

<210> SEQ ID NO 28
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is N-methyl-glutamic acid
<220> FEATURE:
<221> NAME/KEY: MISC_FEATURE
<222> LOCATION: (6)..(6)
<223> OTHER INFORMATION: Xaa at position 6 is norleucine
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
<222> LOCATION: (9)..(9)
<223> OTHER INFORMATION: Xaa at position 9 is N-methyl-glutamic acid

<400> SEQUENCE: 28

Xaa Gln Gly Ala Glu Xaa Ser Asn Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is isoglutamine
<220> FEATURE:
<221> NAME/KEY: MISC_FEATURE
<222> LOCATION: (4)..(4)
<223> OTHER INFORMATION: Xaa at position 4 is beta-alanine
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
```

```
<222> LOCATION: (9)..(9)
<223> OTHER INFORMATION: Xaa at position 9 is glutamic acid methyl ester

<400> SEQUENCE: 29

Xaa Gln Gly Xaa Glu Leu Ser Asn Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (9)..(9)
<223> OTHER INFORMATION: The C-terminal amino acid at position 9 is
      optionally amidated

<400> SEQUENCE: 30

Gln Gly Ala Glu Leu Ser Asn Glu Glu
1               5

<210> SEQ ID NO 31
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-asparagine
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
<222> LOCATION: (9)..(9)
<223> OTHER INFORMATION: Xaa at position 9 is N-methyl-glutamic acid

<400> SEQUENCE: 31

Xaa Gly Ala Glu Xaa Ser Asn Glu Xaa
1               5

<210> SEQ ID NO 32
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is isoglutamine
<220> FEATURE:
<221> NAME/KEY: MISC_FEATURE
<222> LOCATION: (3)..(3)
<223> OTHER INFORMATION: Xaa at position 3 is beta-alanine
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
<222> LOCATION: (9)..(9)
```

```
<223> OTHER INFORMATION: Xaa at position 9 is glutamic acid methyl ester

<400> SEQUENCE: 32

Xaa Gly Xaa Glu Leu Ser Asn Glu Xaa
1               5

<210> SEQ ID NO 33
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MOD_RES
<222> LOCATION: (9)..(9)
<223> OTHER INFORMATION: The C-terminal amino acid at position 9 is
      optionally amidated

<400> SEQUENCE: 33

Gly Ala Glu Leu Ser Asn Glu Glu Arg
1               5

<210> SEQ ID NO 34
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is norvaline
<220> FEATURE:
<221> NAME/KEY: MISC_FEATURE
<222> LOCATION: (4)..(4)
<223> OTHER INFORMATION: Xaa at position 4 is norleucine
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
<222> LOCATION: (9)..(9)
<223> OTHER INFORMATION: Xaa at position 9 is ornithine

<400> SEQUENCE: 34

Xaa Ala Glu Xaa Ser Asn Glu Glu Xaa
1               5

<210> SEQ ID NO 35
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is beta-alanine
<220> FEATURE:
<221> NAME/KEY: MISC_FEATURE
<222> LOCATION: (5)..(5)
<223> OTHER INFORMATION: Xaa at position 5 is D-serine
<220> FEATURE:
<221> NAME/KEY: MOD_RES
<222> LOCATION: (9)..(9)
<223> OTHER INFORMATION: The C-terminal amino acid at position 9 is
      optionally amidated
<220> FEATURE:
<221> NAME/KEY: MISC_FEATURE
<222> LOCATION: (9)..(9)
<223> OTHER INFORMATION: Xaa at position 9 is N-methyl arginine
```

```
<400> SEQUENCE: 35

Xaa Ala Glu Leu Xaa Asn Glu Glu Xaa
1               5
```

PEPTIDES FOR DRY EYE DISEASE

CROSS-REFERENCES TO RELATED APPLICATIONS

This application claims priority to U.S. Provisional Application No. 62/469,170, filed Mar. 9, 2017, the disclosure is hereby incorporated by reference in its entirety for all purposes.

REFERENCE TO A SEQUENCE LISTING SUBMITTED VIA EFS-WEB

The content of the ASCII text file of the sequence listing named "Ally001PCT_ST25" which is 19 kb in size was created on Mar. 5, 2018 and electronically submitted via EFS-Web herewith the application is incorporated herein by reference in its entirety.

FIELD

The present teachings relate to peptides that are involved in the inhibition of trans-endothelial migration of T cells in response to inflammatory processes. Treatments for subjects suffering from dry eye and ocular diseases and disorders can be developed using the compositions and methods comprising a peptide, analogue, variant, derivative or pharmaceutically acceptable salt thereof.

BACKGROUND

The ocular surface system consists of the cornea, conjunctiva, lacrimal glands, Meibomian glands, nasolacrimal duct, and their associated tear and connective tissue matrices, as well as the eyelids and eyelashes, all integrated by continuous epithelia and interconnected nervous, endocrine, immune, and vascular systems. The lacrimal glands produce human tears. Tears are distributed by blinking, undergo evaporation from the ocular surface, and drain through the nasal lacrimal duct. Exposure of ocular surface epithelial cells to elevated tear osmolality activates inflammatory pathways including the release of pro-inflammatory cytokines. This can lead to the recruitment and infiltration of immune cells to the ocular surface, particularly antigen presenting cells and T cells.

Dry eye disease (DED or dry eye), also known as keratoconjunctivitis sicca, is a multifactorial disorder of the tears and ocular surface. It is characterized by symptoms including dry irritated eyes, excessively watery eyes, burning and stinging, light sensitivity, a foreign body sensation, pain and redness, eye fatigue, and/or blurred vision. In dry eye the ocular surface epithelium undergoes squamous metaplasia, manifested by loss of goblet cells, mucin deficiency and keratinization, resulting in tear film instability. Factors that adversely affect tear film stability and osmolality can induce ocular surface damage and initiate an inflammatory cascade that generates innate and adaptive immune responses. These immuno-inflammatory responses lead to further ocular surface damage and the development of a self-perpetuating inflammatory cycle (Stevenson et al., Arch Ophthalmol. 2012, 130(i):90-100).

The major classes of dry eye are aqueous tear-deficient dry eye (ADDE) and evaporative dry eye (EDE). ADDE is due to failure of lacrimal tear secretion and this class can be further subdivided to Sjogren's syndrome dry eye (the lacrimal and salivary glands are targeted by an autoimmune process, e.g., rheumatoid arthritis) and non-Sjogren's syndrome dry eye (lacrimal dysfunction, but the systemic autoimmune features of Sjogren's syndrome are excluded, e.g., age-related dry eye). EDE is due to excessive water loss from the exposed ocular surface in the presence of normal lacrimal secretory function. Its causes can be intrinsic (due to intrinsic disease affecting lid structures or dynamics, e.g., Meibomian gland dysfunction) or extrinsic (where ocular surface disease occurs due to some extrinsic exposure, e.g., vitamin A deficiency). With Meibomian gland dysfunction, the lipid layer of tears is altered, causing increased tear evaporation. {See, e.g., "The Definition and Classification of Dry Eye Disease: Guidelines from the 2007 International Dry Eye Work Shop," Ocul Surf, 2007, 5(2): 75-92). In both classes of dry eye, the end result is a self-perpetuating cycle of irritation and inflammation.

It is estimated that almost 5 million Americans 50 years and older have DED, and millions more experience episodic symptoms of dry eye; of these, approximately two-thirds are women. The prevalence of DED rises dramatically with increasing age. Dry eye disease can hinder the performance of activities of daily living, and DED is associated with an overall decrease in quality of life.

There are several techniques or clinical measures used for diagnosing and evaluating the severity of a patients dry eye, including the Ocular Surface Disease Index (OSDI) questionnaire, the Symptom Assessment in Dry Eye (SADE), Tear Break-up Time (TBUT), vital dye staining of the ocular surface, tear meniscus height analysis, tear film osmolarity analysis, the Schirmer's Test, and the like. The TBUT test measures the time required for the three-layer tear film to break up. A shortened TBUT test time indicates a decreased quality of tears and is indicative of dry eye. The Schirmer's Test measures the volume of tears produced, and is performed by of placing a small strip of filter paper inside the lower eyelid (conjunctival sac) of each eye for several minutes, allowing tear fluid to be drawn into the filter paper by capillary action. The paper is then removed and the amount of moisture is measured in millimeters. Typically, measurement of less than 5 mm indicates dry eye.

Ophthalmologists who treat chronic DED patients have to manage the symptoms of ocular surface inflammation. Apart from reducing vision, the symptoms of such inflammation also include redness, pain, swelling, edema (chemosis) of the conjunctiva and eyelids. In DED, the irritative symptoms may be due to the release of pro-inflammatory cytokines (Lam et al, Am J Ophthalmol, 2009, 147: 198-205; Albersmeyer et al., Exp Eye Res, 2010, 90(3):444-451) and infiltration of inflammatory cells (Kunert et al, Arch. Ophthalmol. 2000, 118-(11): 1489-96) on the ocular surface, as well as stimulation of the nerve fibers innervating the ocular surface, resulting ocular surface tissue damage. Inflammation also leads to epitheliopathy, the key clinical sign identified in DED.

Current therapies for dry eye are palliative with a focus on the replacement of tears to reduce symptoms. Conventional treatment of mild and moderate cases of dry eye includes supplemental lubrication. Application of ophthalmic formulations, such as therapeutic eye drops and artificial tears, every few hours can aid in maintaining and strengthening the tear film on the ocular surface and provide temporary relief. Lubricating tear ointments are also used. Tear ointments contain white petrolatum, mineral oil, and similar lubricants, and serve as a lubricant and an emollient. While these palliative therapies have benefits over the short term, they have limited utility in long-term control therapy for dry eye.

RESTASIS® (cyclosporine A) is the first prescription product for dry eye therapy. Cyclosporine A exerts immunosuppressive activity through several pathways and the immunomodulatory activity of cyclosporine A is used in the treatment of immune-based disorders, such as transplant rejection, psoriasis, ulcerative colitis, rheumatoid arthritis, and DED. Topical administration of cyclosporine A has been shown to increase tear fluid secretion, possibly by promoting the local release of parasympathetic nervous system-associated neurotransmitters. The beneficial effects of cyclosporine A treatment in DED are well established; however, it is clear that many patients with DED do not show a consistent therapeutic response to topical cyclosporine A.

Thus, there are currently few effective therapeutic options for the majority of patients with dry eye and ocular diseases associated with inflammation. Surprisingly, the disclosed modified peptides can be shown to inhibit T cell migration in response to inflammation in ocular diseases. As such, there is a high unmet need for effective and safe therapies. The present invention satisfies this need and provides other advantages as well.

SUMMARY

In one aspect, provided herein are compositions and methods for treating dry eye and ocular diseases associated with inflammation in a subject in need thereof. The method comprises administering to the subject a therapeutically effective amount of a composition comprising a peptide compound referred to as peptide inhibitors of trans-endothelial migration of T cells or a pharmaceutically acceptable salt thereof, and a pharmaceutically acceptable excipient to treat ocular diseases associated with inflammation in the subject. In some embodiments, the composition includes two or more different, e.g., 2, 3, 4, 5, 6, 7, 8, 9, 10 or more different peptides or analogues thereof or pharmaceutically acceptable salts thereof.

In some embodiments, the peptide is represented by the peptide sequences as illustrated below in Table 1. In one embodiment included are analogues, variants, derivatives, and pharmaceutically acceptable salts thereof of the peptides of Table 1. In one embodiment, the ophthalmic composition comprises a peptide selected from the group consisting of SEQ ID NO:1 to SEQ ID NO:35, including an analogue thereof, a variant thereof and a derivative thereof. In one embodiment a polynucleotide sequence encodes the peptide of any one of SEQ ID NO:1 to SEQ ID NO:35. The polynucleotide encoding the peptide can be the DNA form or DNA/RNA hybrid forms thereof; and any complementary sequence thereof. In one embodiment, the ophthalmic composition has a peptide or analogue thereof of the peptides in Table 1 or a polynucleotide sequence encoding the peptide of any one of SEQ ID NO:1 to SEQ ID NO:35. The polynucleotide encoding the peptide can be the DNA form or DNA/RNA hybrid forms thereof; and any complementary sequence thereof. In one embodiment the peptide is a synthetic peptide.

In another embodiment, the present invention is a composition comprising one or more peptides comprising a peptide selected from the group consisting of H-Ser-Val-Thr-Glu-Gln-Gly-Ala-Glu-Leu-Ser-Asn-Glu-Glu-Arg-NH2 (SEQ ID NO:1), H-DSer-Val-AlloThr-Glu-Gln-Gly-Ala-Glu-Nle-Ser-Asn-NMeGlu-Glu-Orn-NH2 (SEQ ID NO:2), H-Hyp-Val-Thr-NMeGlu-Gln-Gly-Ala-Glu-Leu-Hyp-DAsn-Glu-Glu-Aha-NH2 (SEQ ID NO:3), H-Ser-Val-Thr-Glu-Gln-Gly-Ala-Glu-Leu-Ser-Asn-Glu-Glu-NH2 (SEQ ID NO:4), H-DSer-Val-AlloThr-Glu-Gln-Gly-Ala-Glu-Nle-Ser-Asn-NMeGlu-GluOMe-NH2 (SEQ ID NO:5), H-Val-Thr-Glu-Gln-Gly-Ala-Glu-Leu-Ser-Asn-Glu-Glu-Arg-NH2 (SEQ ID NO:6), H-Nva-AlloThr-Glu-Gln-Gly-Ala-Glu-Nle-Ser-Asn-NMeGlu-Glu-Orn-NH2 (SEQ ID NO:7), H-Val-Thr-Glu-Gln-Gly-Ala-Glu-Leu-Ser-Asn-Glu-Glu-NH2 (SEQ ID NO:8), H-Nva-AlloThr-Glu-Gln-Gly-Ala-Glu-Nle-Ser-Asn-NMeGlu-GluOMe-NH2 (SEQ ID NO:9), H-Chex-Thr-NMeGlu-Gln-Gly-Ala-Glu-Leu-Hyp-DAsn-Glu-DGln-NH2 (SEQ ID NO:10), H-Val-Thr-Glu-Gln-Gly-Ala-Glu-Leu-Ser-Asn-Glu-NH2 (SEQ ID NO:11), H-Nva-AlloThr-Glu-Gln-Gly-Ala-Glu-Nle-Ser-Asn-NMeGlu-NH2 (SEQ ID NO:12), H-Thr-Glu-Gln-Gly-Ala-Glu-Leu-Ser-Asn-Glu-Glu-NH2 (SEQ ID NO:13), H-AlloThr-Glu-Gln-Gly-Ala-Glu-Nle-Ser-Asn-NMeGlu-GluOMe-NH2 (SEQ ID NO:14), H-Thr-Glu-Gln-Gly-Ala-Glu-Leu-Ser-Asn-Glu-NH2 (SEQ ID NO:15), H-AlloThr-Glu-Gln-Nva-Ala-Glu-Nle-Ser-Asn-NMeGlu-NH2 (SEQ ID NO:16), H-DSer-Glu-Gln-Gly-Ala-Glu-Leu-DSer-DAsn-DGln-NH2 (SEQ ID NO:17), H-Ser-Val-Thr-Glu-Gln-Gly-Ala-Glu-Leu-NH2 (SEQ ID NO:18), H-DSer-Val-Thr-Glu-Gln-Nva-Ala-Glu-Nle-NH2 (SEQ ID NO:19), H-Hyp-Val-Thr-Glu-Gln-Gly-βAla-Glu-Aha-NH2 (SEQ ID NO:20), H-Val-Thr-Glu-Gln-Gly-Ala-Glu-Leu-Ser-NH2 (SEQ ID NO:21), H-Nva-Thr-Glu-Gln-Nva-Ala-Glu-Leu-DSer-NH2 (SEQ ID NO:22), H-Chex-Thr-Glu-Gln-Gly-βAla-Glu-Leu-Hyp-NH2 (SEQ ID NO:23), H-Thr-Glu-Gln-Gly-Ala-Glu-Leu-Ser-Asn-NH2 (SEQ ID NO:24), H-AlloThr-Glu-Gln-Nva-Ala-Glu-Leu-Ser-DAsn-NH2 (SEQ ID NO:25), H-DSer-Glu-Gln-Gly-βAla-Glu-Leu-Ser-DGln-NH2 (SEQ ID NO:26), H-Glu-Gln-Gly-Ala-Glu-Leu-Ser-Asn-Glu-NH2 (SEQ ID NO:27), H-NMeGlu-Gln-Gly-Ala-Glu-Nle-Ser-Asn-NMeGlu-NH2 (SEQ ID NO:28), H-IsoGln-Gln-Gly-βAla-Glu-Leu-Ser-Asn-GluOMe-NH2 (SEQ ID NO:29), H-Gln-Gly-Ala-Glu-Leu-Ser-Asn-Glu-Glu-NH2 (SEQ ID NO:30), H-DAsn-Gly-Ala-Glu-Nle-Ser-Asn-Glu-NMeGlu-NH2 (SEQ ID NO:31), H-IsoGln-Gly-βAla-Glu-Leu-Ser-Asn-Glu-GluOMe-NH2 (SEQ ID NO:32), H-Gly-Ala-Glu-Leu-Ser-Asn-Glu-Glu-Arg-NH2 (SEQ ID NO:33), H-Nva-Ala-Glu-Nle-Ser-Asn-Glu-Glu-Orn-NH2 (SEQ ID NO:34), and H-βAla-Ala-Glu-Leu-DSer-Asn-Glu-Glu-NMeArg-NH2 (SEQ ID NO:35), an analogue thereof, a variant thereof, and a derivative thereof.

In yet another invention, the present invention is a composition of one or more peptides consisting of a peptide selected from the group consisting of H-Ser-Val-Thr-Glu-Gln-Gly-Ala-Glu-Leu-Ser-Asn-Glu-Glu-Arg-NH2 (SEQ ID NO:1), H-DSer-Val-AlloThr-Glu-Gln-Gly-Ala-Glu-Nle-Ser-Asn-NMeGlu-Glu-Orn-NH2 (SEQ ID NO:2), H-Hyp-Val-Thr-NMeGlu-Gln-Gly-Ala-Glu-Leu-Hyp-DAsn-Glu-Glu-Aha-NH2 (SEQ ID NO:3), H-Ser-Val-Thr-Glu-Gln-Gly-Ala-Glu-Leu-Ser-Asn-Glu-Glu-NH2 (SEQ ID NO:4), H-DSer-Val-AlloThr-Glu-Gln-Gly-Ala-Glu-Nle-Ser-Asn-NMeGlu-GluOMe-NH2 (SEQ ID NO:5), H-Val-Thr-Glu-Gln-Gly-Ala-Glu-Leu-Ser-Asn-Glu-Glu-Arg-NH2 (SEQ ID NO:6), H-Nva-AlloThr-Glu-Gln-Gly-Ala-Glu-Nle-Ser-Asn-NMeGlu-Glu-Orn-NH2 (SEQ ID NO:7), H-Val-Thr-Glu-Gln-Gly-Ala-Glu-Leu-Ser-Asn-Glu-Glu-NH2 (SEQ ID NO:8), H-Nva-AlloThr-Glu-Gln-Gly-Ala-Glu-Nle-Ser-Asn-NMeGlu-GluOMe-NH2 (SEQ ID NO:9), H-Chex-Thr-NMeGlu-Gln-Gly-Ala-Glu-Leu-Hyp-DAsn-Glu-DGln-NH2 (SEQ ID NO:10), H-Val-Thr-Glu-Gln-Gly-Ala-Glu-Leu-Ser-Asn-Glu-NH2 (SEQ ID NO:11), H-Nva-AlloThr-Glu-Gln-Gly-Ala-Glu-Nle-Ser-Asn-NMeGlu-NH2 (SEQ ID NO:12), H-Thr-Glu-Gln-Gly-Ala-Glu-Leu-Ser-Asn-Glu-Glu-NH2 (SEQ ID NO:13), H-AlloThr-Glu-Gln-Gly-Ala-Glu-Nle-Ser-Asn-NMeGlu-GluOMe-NH2 (SEQ ID NO:14), H-Thr-Glu-Gln-Gly-Ala-Glu-Leu-Ser-Asn-Glu-NH2 (SEQ ID NO:15), H-AlloThr-Glu-Gln-Nva-Ala-Glu-Nle-Ser-Asn-NMeGlu-NH2 (SEQ ID NO:16), H-DSer-Glu-Gln-Gly-Ala-Glu-Leu-DSer-DAsn-DGln-NH2 (SEQ ID NO:17), H-Ser-Val-Thr-Glu-Gln-Gly-Ala-Glu-Leu-NH2 (SEQ ID NO:18), H-DSer-Val-Thr-Glu-Gln-Nva-Ala-Glu-Nle-NH2 (SEQ ID NO:19), H-Hyp-Val-Thr-Glu-Gln-Gly-βAla-Glu-Aha-NH2 (SEQ ID NO:20), H-Val-Thr-Glu-Gln-Gly-Ala-Glu-Leu-Ser-NH2 (SEQ ID NO:21), H-Nva-Thr-Glu-Gln-Nva-Ala-Glu-Leu-DSer-NH2 (SEQ ID NO:22), H-Chex-Thr-Glu-Gln-Gly-βAla-Glu-Leu-Hyp-NH2 (SEQ ID NO:23), H-Thr-Glu-Gln-Gly-Ala-Glu-Leu-Ser-Asn-NH2 (SEQ ID NO:24), H-AlloThr-Glu-Gln-Nva-Ala-Glu-Leu-Ser-DAsn-NH2 (SEQ ID NO:25), H-DSer-Glu-Gln-Gly-βAla-Glu-Leu-Ser-DGln-NH2 (SEQ ID NO:26), H-Glu-Gln-Gly-Ala-Glu-Leu-Ser-Asn-Glu-NH2 (SEQ ID NO:27), H-NMeGlu-Gln-Gly-Ala-Glu-Nle-Ser-Asn-NMe-Glu-NH2 (SEQ ID NO:28), H-IsoGln-Gln-Gly-βAla-Glu-Leu-Ser-Asn-GluOMe-NH2 (SEQ ID NO:29), H-Gln-Gly-Ala-Glu-Leu-Ser-Asn-Glu-Glu-NH2 (SEQ ID NO:30), H-DAsn-Gly-Ala-Glu-Nle-Ser-Asn-Glu-NMeGlu-NH2 (SEQ ID NO:31), H-IsoGln-Gly-βAla-Glu-Leu-Ser-Asn-Glu-GluOMe-NH2 (SEQ ID NO:32), H-Gly-Ala-Glu-Leu-Ser-Asn-Glu-Arg-NH2 (SEQ ID NO:33), H-Nva-Ala-Glu-Nle-Ser-Asn-Glu-Glu-Orn-NH2 (SEQ ID NO:34), and H-βAla-Ala-Glu-Leu-DSer-Asn-Glu-Glu-NMeArg-NH2 (SEQ ID NO:35), an analogue thereof, a variant thereof, and a derivative thereof.

In one aspect, provided is a pharmaceutical composition comprising at least one peptide compound of Table 1, or a pharmaceutically active salt thereof; and a pharmaceutically acceptable excipient. The pharmaceutical composition with the at least one peptide compound of Table 1, or a pharmaceutically active salt thereof can be present in the composition in an amount sufficient to improve tear film stability when the pharmaceutical composition is administered to the subject in need thereof. In one embodiment the pharmaceutically acceptable excipient can comprise at least one of a solvent, a buffering agent, a preservative, a chelating agent, an antioxidant, a stabilizer, an emulsifying agent, a suspending agent, and a diluent. In one embodiment the composition further has 1.0% to 10.0% Lifitegrast or a salt thereof.

In some embodiments, the composition can be used to treat dry eye having at least one symptom of dry eye is selected from the group consisting of: redness, discharge, excessive tearing, inability to produce tears, dryness, irritation, itchiness, pain, discomfort, inflammation, fatigue, foreign body sensation, light sensitivity, blurred vision, and any combination thereof of the eye, stinging, burning or scratchy sensation in the eye; ocular dryness or grittiness; stringy mucus in or around the eye; increase eye irritation; eye fatigue; sensitivity to light (photophobia); eye redness; excessive tearing; episode of blurred vision; foreign body sensation in the eye; pain or soreness around or in the eye; inability to cry when emotionally stressed; decreased tolerance of an activity requiring sustained visual attention; and any combination thereof. In some embodiments, the dry eye presents at least one symptom or clinical sign of dry eye including but not limited to a change in tear secretion, a change in tear clearance, ocular surface damage, corneal epithelial defects, a change in ocular surface cells, a change in tear film stability, a change in tear volume, a change in tear film composition, a change in tear osmolarity, and any combination thereof. In some embodiments, the dry eye is selected from the group consisting of hypolacrimation, tear deficiency, xerophthalmia, Sjogren's syndrome dry eye, non-Sjogren's syndrome dry eye, keratoconjunctivitis sicca, aqueous tear-deficiency dry eye (ADDE), evaporative dry eye (EDE), environmental dry eye, Stevens-Johnson syndrome, ocular pemphigoid, blepharitis marginal, eyelid-closure failure, sensory nerve paralysis, allergic conjunctivitis-associated dry eye, post-viral conjunctivitis dry eye, post-cataract surgery dry eye, VDT operation-associated dry eye, and contact lens wearing-associated dry eye. In one embodiment, the dry eye is an ocular disease associated with inflammation selected from the group consisting of uveitis, scleritis, post-eye surgery inflammation, corneal transplantation, corneal wound healing, conjunctivitis, retinal disease, glaucoma, ocular hypertension, pterygium and a combination thereof.

In some embodiments the composition for treatment of dry eye can be administered topically, by intravitreal injection, by subconjunctival injection, by conjunctival injection, by intramuscular injection, by subcutaneous injection, by intravenous injection, by intracameral injection, or by implantation into the subjects eye. In some embodiments, the composition is in a formulation selected from the group consisting of a solution, suspension, syrup, liquid, gel, hydrogel, emulsion, liposome, aerosol, mist, film, suspension, plug, polymer, implant, contact lens, ocular insert, nanoparticle, microparticle, a sustained release formulation, and a formulation suitable for an ocular medical device. In some embodiments, the peptide compound is present in an amount between about 0.01% (wt) to about 5.0% (wt) of the final composition. In some embodiments, the composition is administered to the subject once a day, two times a day, three times a day or more often (more frequently). In other embodiments, the composition is administered every other day or less often (less frequently). In some embodiments, the subject in need thereof can further receive a composition comprising cyclosporine, artificial tears, lifitegrast, tavilermide, a corticosteroid, an anti-inflammatory agent, or any combination thereof.

In another aspect, provided herein is a method for treating dry eye in a subject in need thereof. The method comprises administering to the subject a therapeutically effective amount of a composition comprising at least one peptide of Table 1 or a pharmaceutically salt thereof and a pharmaceutically acceptable excipient to treat dry eye in the subject. In some embodiments, the peptide can be administered topically, by intravitreal injection, by subconjunctival injection, by conjunctival injection, by intramuscular injection, by subcutaneous injection, by intravenous injection, by intracameral injection, or by implantation into the subjects eye. In some embodiments, the dry eye presents at least one symptom or clinical sign of dry eye diseases selected from the group consisting hypolacrimation, tear deficiency, xerophthalmia, Sjogren's syndrome dry eye, non-Sjogren's syndrome dry eye, keratoconjunctivitis sicca, aqueous tear-deficiency dry eye (ADDE), evaporative dry eye (EDE), environmental dry eye, Stevens-Johnson syndrome, ocular pemphigoid, blepharitis marginal, eyelid-closure failure, sensory nerve paralysis, allergic conjunctivitis-associated dry eye, post-viral conjunctivitis dry eye, post-cataract surgery dry eye, VDT operation-associated dry eye, and contact lens wearing-associated dry eye.

In one embodiment the composition further has 1.0% to 10.0% Lifitegrast or a salt thereof. In some embodiments, the composition is administered to the subject once a day, two times a day, three times a day or more often (more frequently). In other embodiments, the composition is administered every other day or less often (less frequently). In some embodiments, the peptide compound is present in an amount between about 0.01% (wt) to about 5.0% (wt) of the final composition. In some embodiments, the subject in need thereof can further receive a composition comprising cyclosporine, artificial tears, a corticosteroid, an anti-inflammatory agent, or any combination thereof. In one embodiment, the method administers a peptide selected from the group consisting of SEQ ID NO:1 to SEQ ID NO:35, an analogue thereof, a variant thereof, a derivative thereof, or a pharmaceutically acceptable salt thereof. In another embodiment the method utilizes a polynucleotide sequence encoding the peptide of any one of SEQ ID NO:1 to SEQ ID NO:35. The polynucleotide encoding the peptide can be the DNA form or DNA/RNA hybrid forms thereof; and any complementary sequence thereof. In one embodiment, the method administers a pharmaceutically acceptable composition comprising the peptide or analogue thereof of SEQ ID NO:1 to SEQ ID NO:35. In one embodiment the peptide is a synthetic peptide.

In one embodiment, the method alleviates or treats at least one symptom of dry eye is selected from the group consisting of redness, discharge, excessive tearing, inability to produce tears, dryness, irritation, itchiness, pain, discomfort, inflammation, fatigue, foreign body sensation, light sensitivity, blurred vision, and any combination thereof of the eye. In some embodiments, the dry eye presents at least one symptom or clinical sign of dry eye including but not limited to a change in tear secretion, a change in tear clearance, ocular surface damage, corneal epithelial defects, a change in ocular surface cells, a change in tear film stability, a change in tear volume, a change in tear film composition, a change in tear osmolarity, and any combination thereof. In some embodiments, the dry eye presents at least one symptom or clinical sign of dry eye diseases selected from the group consisting hypolacrimation, tear deficiency, xerophthalmia, Sjogren's syndrome dry eye, non-Sjogren's syndrome dry eye, keratoconjunctivitis sicca, aqueous tear-deficiency dry eye (ADDE), evaporative dry eye (EDE), environmental dry eye, Stevens-Johnson syndrome, ocular pemphigoid, blepharitis marginal, eyelid-closure failure, sensory nerve paralysis, allergic conjunctivitis-associated dry eye, post-viral conjunctivitis dry eye, post-cataract surgery dry eye, VDT operation-associated dry eye, and contact lens wearing-associated dry eye. In one embodiment, the dry eye is an ocular disease associated with inflammation selected from the group consisting of uveitis, scleritis, post-eye surgery inflammation, corneal transplantation, corneal wound healing, conjunctivitis, retinal disease, glaucoma, ocular hypertension, pterygium and a combination thereof.

In yet another aspect, provided herein is a method for treating an ocular disease associated with inflammation in a subject in need thereof. The method comprises administering to the subject a therapeutically effective amount of a composition comprising a peptide compound or a pharmaceutically acceptable salt thereof, and a pharmaceutically acceptable excipient to treat the ocular disease associated with inflammation in the subject. In some embodiments, the composition includes two or more, e.g., 2, 3, 4, 5, 6, 7, 8, 9, 10 or more different peptides or analogues thereof or pharmaceutically acceptable salts thereof. In some embodiments, the ocular disease associated with inflammation is selected from the group consisting of uveitis, scleritis, post-eye surgery inflammation, corneal transplantation, corneal wound healing, conjunctivitis, retinal disease, glaucoma, ocular hypertension, pterygium and a combination thereof.

In another aspect, provided herein is a method for alleviating at least one symptom or clinical sign of dry eye in a subject in need thereof. The method comprises administering to the subject a therapeutically effective amount of a composition comprising a peptide compound or a pharmaceutically acceptable salt thereof, and a pharmaceutically acceptable excipient to alleviate at least one symptom or clinical sign of dry eye in the subject. In some embodiments, the composition includes two or more different, e.g., 2, 3, 4, 5, 6, 7, 8, 9, 10 or more different peptide compounds or pharmaceutically acceptable salts thereof.

In another aspect, provided herein is a method for treating an ocular disease associated with inflammation in a subject in need thereof. The method comprises administering to the subject a therapeutically effective amount of a composition comprising a peptide compound or a pharmaceutically acceptable salt thereof, and a pharmaceutically acceptable excipient to treat the ocular disease associated with inflammation in the subject. In some embodiments, the composition includes two or more different, e.g., 2, 3, 4, 5, 6, 7, 8, 9, 10 or more different peptide compounds or pharmaceutically acceptable salts thereof.

In one embodiment, the method for alleviating at least one symptom or clinical sign of dry eye or for treating an ocular disease can be administered topically, by intravitreal injection, by subconjunctival injection, by conjunctival injection, by intramuscular injection, by subcutaneous injection, by intravenous injection, by intracameral injection, or by implantation into the subjects eye. In one embodiment, the method for alleviating at least one symptom or clinical sign of dry eye or for treating an ocular disease is selected from the group consisting of hypolacrimation, tear deficiency, xerophthalmia, Sjogren's syndrome dry eye, non-Sjogren's syndrome dry eye, keratoconjunctivitis sicca, aqueous tear-deficiency dry eye (ADDE), evaporative dry eye (EDE), environmental dry eye, Stevens-Johnson syndrome, ocular pemphigoid blepharitis marginal, eyelid-closure failure, sensory nerve paralysis, allergic conjunctivitis-associated dry eye, post-viral conjunctivitis dry eye, post-cataract surgery dry eye, VDT operation-associated dry eye, and contact lens wearing-associated dry eye. In one embodiment, the method for alleviating at least one symptom or clinical sign of dry eye or for treating an ocular disease comprises at least one symptom of dry eye selected from the group consisting of redness, discharge, excessive tearing, inability to produce tears, dryness, irritation, itchiness, pain, discomfort, inflammation, fatigue, foreign body sensation, light sensitivity, blurred vision, and any combination thereof of the eye. In some embodiments, at least one clinical sign of dry eye is selected from the group consisting of a change in tear secretion, a change in tear clearance, a change in tear osmolarity, ocular surface damage, corneal epithelial defects, a change in ocular surface cells, a change in tear film stability, a change in tear volume, a change in tear film composition, a change in goblet cell or Meibomian or lacrimal gland physiology, appearance, number, or function and any combination thereof.

In some embodiments, the method for alleviating at least one symptom or clinical sign of dry eye or for treating an ocular disease in which the composition can be administered in a formulation selected from the group consisting of a solution, suspension, syrup, liquid, gel, hydrogel, emulsion, liposome, aerosol, mist, film, suspension, plug, polymer, implant, contact lens, ocular insert, nanoparticle, microparticle, a sustained release formulation, and a formulation suitable for an ocular medical device. In some embodiments, the peptide compound is present in an amount between about 0.01% (wt) to about 5.0% (wt) of the final composition. In some embodiments, the composition is administered to the subject once a day, two times a day, three times a day or more often (more frequently). In other embodiments, the composition is administered every other day or less often (less frequently). In some embodiments, the subject in need thereof can further receive a composition comprising cyclosporine, artificial tears, a corticosteroid, an anti-inflammatory agent, or any combination thereof. In one embodiment the methods for treating dry eye further comprises administering to the subject a therapeutically effective amount of a peptide composition further having about 1.0% to about 10.0% Lifitegrast.

In one embodiment, the method for alleviating at least one symptom or clinical sign of dry eye or for treating an ocular disease comprises administering a peptide selected from the group consisting of SEQ ID NO:1 to SEQ ID NO:35, an analogue thereof, a variant thereof, a derivative thereof, or a pharmaceutically acceptable salt thereof. In one embodiment, the peptide or an analogue thereof can be administered as a pharmaceutically acceptable composition. In one embodiment, the peptide or an analogue thereof can be used for alleviating at least one symptom or clinical sign of dry eye or for treating an ocular disease.

BRIEF DESCRIPTION OF THE DRAWINGS

FIG. 4A-4E provides scatter plots illustrating the change in activated T cell presence when dry eye presents within the conjunctiva and 10 days after treatment. FIG. 4A represents the scatter plot of activated T cell level of normal (UT) eye; FIG. 4B represents the scatter plots of activated T cell level of dry eye (Vehicle); FIG. 4C represents scatter plots of activated T cell level after administration of 5% Lifitegrast; FIG. 4D represents scatter plots of activated T cell level after administration of 0.1% SEQ ID NO:1, a peptide inhibitor of trans-endothelial migration.

DETAILED DESCRIPTION OF VARIOUS EMBODIMENTS

Figure 1:
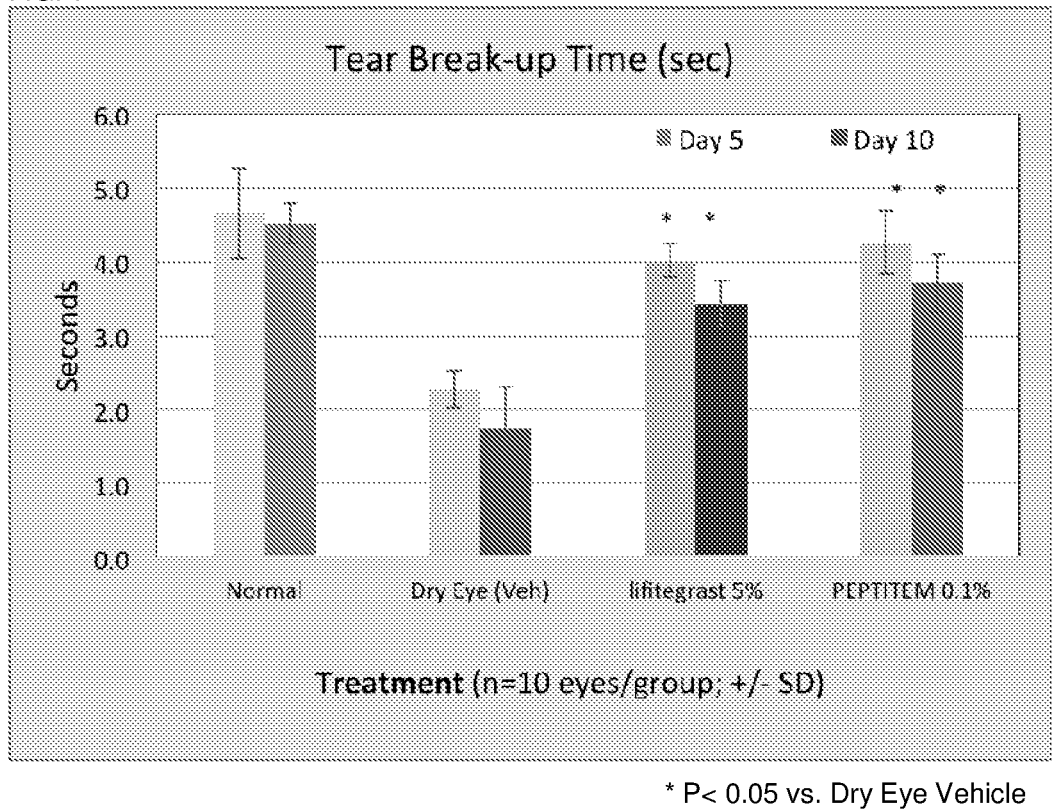
FIG. 1 is a bar chart illustrating the change in tear film break-up time when a dry eye is treated with either 5% Lifitegrast or 0.1% SEQ ID NO:1, a peptide inhibitor of trans-endothelial migration (PEPITEM) at five and ten days post treatment.

Disclosed herein are embodiments of compositions, methods and kits for treating dry eye or an ocular disease associated with inflammation in a subject in need thereof. The method includes administering to said subject a therapeutically effective composition comprising a peptide compound or a pharmaceutically acceptable salt thereof, and a pharmaceutically acceptable excipient. Also provided herein are methods for alleviating at least one symptom or clinical sign of dry eye in a subject. In some embodiments, the therapeutically effective composition comprises at least two different peptide compounds or pharmaceutically acceptable salts thereof. The invention is based, in part, on the discovery that administration to the eye of a peptide compound or a pharmaceutically acceptable salt thereof increases tear volume and reduces corneal surface irregularities in subjects with dry eye.

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "dry eye" refers to a multifactorial disease of the tears and ocular surface (including the cornea, conjunctiva, and eye lids) results in symptoms of discomfort, visual disturbance and tear film instability with potential damage to the ocular surface, as defined by the "The Definition and Classification of Dry Eye Disease: Guidelines from the 2007 International Dry Eye Work Shop," Ocul Surf, 2007, 5(2): 75-92). Dry eye can be accompanied by increased osmolarity of the tear film and inflammation of the ocular surface. Dry eye includes dry eye syndrome, keratoconjunctivitis sicca (KCS), dysfunctional tear syndrome, lacrimal keratoconjunctivitis, evaporative tear deficiency, aqueous tear deficiency, and LASIK-induced neurotrophic epitheliopathy (LE).

The term "ocular disease associated with inflammation" refers to a disease or disorder of the eye wherein inflammation causes damage to the ocular surface system. As used herein, "the ocular surface system" includes the cornea, conjunctiva, lacrimal glands, Meibomian glands, nasolacrimal duct, and their associated tear and connective tissue matrices, as well as the eyelids and eyelashes, all integrated by continuous epithelia and interconnected nervous, endocrine, immune, and vascular systems. Ocular diseases associated with inflammation include, but are not limited to, uveitis, scleritis, post-eye surgery inflammation, corneal transplantation, corneal wound healing, conjunctivitis, retinal disease, glaucoma, ocular hypertension, pterygium, dry eye, keratitis, allergic eye disease, infectious keratitis, herpetic keratitis, corneal angiogenesis, lymphangiogenesis, uveitis, pterygium, retinitis, choroiditis, acute multifocal placoid pigment epitheliopathy, Behcet's disease, post-surgical corneal wound healing, conditions caused by laser, conditions caused by photodynamic therapy, wet and dry age-related macular degeneration (ARMD), conditions affecting the posterior part of the eye, maculopathies, retinal degeneration, non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi and Harada syndrome, retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coats disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease, sympathetic ophthalmia, uveitic retinal disease, retinal detachment, trauma, conditions caused by photodynamic therapy, photocoagulation, hypoperfusion during surgery, radiation retinopathy, and bone marrow transplant retinopathy, proliferative vitreal retinopathy and epiretinal membranes, proliferative diabetic retinopathy, ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, myiasis, retinitis pigmentosa, systemic disorders with accosiated retinal dystrophies, congenital stationary night blindness, cone dystrophies, Stargardt's disease, fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum; retinal detachment, macular hole, giant retinal tear, retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, other diseases affecting the posterior part of the eye, punctate inner choroidopathy, acute posterior multifocal placoid pigment epitheliopathy, myopic retinal degeneration, acute retinal pigment epitheliitis, postsurgical corneal inflammation, blepharitis, MGD, glaucoma, ocular hypertension, branch vein occlusion, retinal diseases, Best's vitelliform macular degeneration, retinitis pigmentosa, proliferative vitreoretinopathy (PVR), and any other degenerative diseases of either the photoreceptors or the retinal pigment epithelial (RPE) and a combination thereof.

The term "therapeutically effective amount," "effective amount" or "therapeutically effective dose" refers to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. In the context of the present invention, the effective amount of a peptide compound can vary depending on co-administration of other therapeutics or disease profile of the individual (among other factors such as age, severity of disease, etc.).

The terms "therapy," "treatment," and "amelioration" refer to any reduction in the severity of symptoms. In the case of treating an ocular disorder, e.g., dry eye, the terms can refer to adding artificial tears, conserving tears, reducing tear evaporation, increasing tear production, reducing inflammation of the eyelids or eye surface, reducing ocular signs to dry eye, etc. As used herein, the terms "treat" and "prevent" are not intended to be absolute terms. Treatment can refer to any delay in onset, amelioration of symptoms, improvement in patient's quality of life, etc. The effect of treatment can be compared to an individual or pool of individuals not receiving the treatment, or to the same patient prior to treatment or at a different time during treatment. In some aspects, the severity of disease is reduced by at least 10%), as compared, e.g., to the individual before administration or to a control individual not undergoing treatment. In some aspects, the severity of disease is reduced by at least 25%, 50%, 75%), 80%), or 90%, or in some cases, no longer detectable using standard diagnostic techniques.

The term "treating" or "treatment" refers to the treating or treatment of a disease or medical condition (such as dry eye or an ocular disease associated with inflammation) in a patient, such as a mammal (particularly a human or an animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating one or more symptoms of the disease or medical condition in a patient. The term encompasses the prophylactic treatment of a disease or condition as to prevent or reduce the risk of acquiring or developing a specific disease or condition, or to prevent or reduce the risk of recurrence.

The term "peptide" refers to an organic compound comprising a chain of two or more amino acids covalently joined by peptide bonds. Peptides may be referred to with respect to the number of constituent amino acids, i.e., a dipeptide contains two amino acid residues, a tripeptide contains three, etc.

The term "amino acid" as used herein means an organic compound containing both a basic amino group and an acidic carboxyl group. Included within this term are natural amino acids {e.g., L-amino acids), modified and unusual amino acids {e.g., D-amino acids), as well as amino acids which are known to occur biologically in free or combined form but usually do not occur in proteins. Included within this term are modified and unusual amino acids, such as those disclosed in, for example, Roberts and Vellaccio (1983) The Peptides, 5: 342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to argininosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, and 3, 3', 5,5'-tetraiodothyronine. Modified or unusual amino acids (all of L-configuration except as noted) which can be used to practice the invention include, but are not limited to, D-amino acids, N-methyl-glutamic acid (NMeGlu), D-serine (DSer), Allo-threonine (AlloThr), hydroxyproline (Hyp), ornithine (Orn), D-asparagine (DAsn), glutamic acid methyl ester (GluOMe), norleucine (Nle), norvaline (Nva), 1-amino-cyclohexyl carboxylic acid (Chex), isoglutamine (IsoGln), β-alanine (βAla), 6-amino-hexanoic acid (Aha), N-methyl arginine (NMeArg), hydroxylysine, 4-hydroxyproline, an N-Cbz-protected amino acid, 2,4-diaminobutyric acid, homoarginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-am inopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "non-natural amino acid" can be used to refer to an amino acid that does not exist on its own in nature, but rather, has been synthesized or created by man. Examples of non-natural amino acids include, but are not limited to, iodinated tyrosine, methylated tyrosine, glycosylated serine, glycosylated threonine, azetidine-2-carboxylic acid, 3,4-dehydroproline, perthiaproline, canavanine, ethionine, norleucine, selenomethionine, aminohexanoic acid, telluromethionine, homoallylglycine, and homopropargylglycine.

The phrase "modified peptide" as used herein, can refer to a peptide from nine to fourteen amino acid residues in length derived from the sequence of SEQ ID NO:1, and retains peptide function, and having at least one substitution, deletion, insertion or replacement amino acid residue selected from of a natural protein occurring amino acid, a natural non-protein amino acid or a modified or unusual amino acid residue as is known to one of skill in the art. SEQ ID NOs:2-35 can be illustrative of modified peptide sequences although the skilled artisan can envision other modified peptide sequences.

Preferred embodiments of the invention are those wherein at least one and up to all amino acid(s) of the nine to fourteen mer length peptide can be replaced by a natural non-protein amino acid, a modified or an unusual and/or non-natural amino acids and which can also include two terminal non-natural amino acid residue replacements in a modified peptide of the invention. Exemplary modified peptides are exhibited in Table 1.

As used herein, "pharmaceutically-acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

The term "pharmaceutically acceptable salt" refers to a derivative of the disclosed compounds wherein the parent compound is modified by making acid or base salts thereof, including acid addition salts and base addition salts. Examples of pharmaceutically-acceptable salts include, but are not limited to, mineral or organic acid salts of basic residues such as amines; alkali or organic salts of acidic residues such as carboxylic acids; and the like. The term "acid addition salt" refers to the corresponding salt derivative of a parent compound that has been prepared by the addition of an acid.

The pharmaceutically acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, adipic, alginic, aspartic, hydroxymaleic, phenylacetic, glutamic, benzoic, salicylic, sulfanilic, 2-acetoxybenzoic, fumaric, benzenesulfonic, toluenesulfonic, methanesulfonic, 2-napthalenesulfonic, ethane disulfonic, oxalic, isethionic, glucoheptanoic, glycerophosphoric, hemisulfanic, heptanoic, hexanoic, hydrochloric, hydrobromic, hydroiodic, 2-hydroxyethanesulfonic, 2-napthalenesulfonic, pectinic, phosphoric, sulfuric, 3-phenylpropionic, picric, pivalic, thiocyanic, p-toluenesulfonic, butyric, camphoric, camphorsulfonic, digluconic, cyclopentanepropionic, bisulfuric, dodecylsulfuric, ethanesulfonic, and undecanoic and the like. Thus, the term "base addition salt" refers to the corresponding salt derivative of a parent compound that has been prepared by the addition of a base. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. The pharmaceutically acceptable salts include the conventional salts or the quaternary ammonium salts of the parent compound formed, for example, from inorganic or organic bases. For example, such conventional salts include, but are not limited to, those derived from inorganic bases such as lithium hydroxide, sodium hydroxide, potassium hydroxide, calcium hydroxide, magnesium hydroxide and ammonium hydroxide and the salts prepared from organic amines, such as methyl amine, ethyl amine, isopropyl amine, piperidine, piperazine, pyrrolidine, ethanolamine, morpholine, diazepine, ethylene diamine, pyridine, quinoline, quinuclidine, and the like.

The term "subject," "individual" or "patient" typically includes humans, but can also include other animals such as, e.g., other primates, rodents, canines, felines, equines, ovines, porcines, and the like.

The term "a symptom" refers to a subjective indication or observation of a disorder or disease experienced or perceived by a patient.

The term "a clinical sign" refers to an objective indication, observation or evidence of a disorder or a disease that may be detected or interpreted by a clinician.

The term "peptide inhibitor of trans-endothelial migration peptide" refers to a polypeptide having a sequence H-Ser-Val-Thr-Glu-Gln-Gly-Ala-Glu-Leu-Ser-Asn-Glu-Glu-Arg-NH$_2$ (SEQ ID NO:1) as well as analogues, variants, derivatives, and pharmaceutically acceptable salts thereof, including but not limited to, the peptides of Table 1 for treating dry eye. Peptides can inhibit the migration of T lymphocytes (T cells), including auto-reactive T cells. The peptide is secreted from B cells and has been shown to have efficacy in the treatment of conditions in which T cell migration is initiated in response to an injury, irritation or inflammatory event. The inventor has been able to show therapeutic utility using the disclosed peptide(s) for the treatment of dry eye or an ocular disease associated with inflammation in a subject in need thereof.

TABLE 1

| Peptide inhibitor of trans-endothelial migration peptide | SEQ ID NO: |
|---|---|
| Peptide and Peptide Derivatives | |
| H-Ser-Val-Thr-Glu-Gln-Gly-Ala-Glu-Leu-Ser-Asn-Glu-Glu-Arg-NH$_2$ | 1 |
| H-DSer-Val-AlloThr-Glu-Gln-Gly-Ala-Glu-Nle-Ser-Asn-NMeGlu-Glu-Orn-NH$_2$ | 2 |
| H-Hyp-Val-Thr-NMeGlu-Gln-Gly-Ala-Glu-Leu-Hyp-DAsn-Glu-Glu-Aha-NH$_2$ | 3 |

TABLE 1-continued

| Peptide inhibitor of trans-endothelial migration peptide | SEQ ID NO: |
|---|---|
| 13 Residue Fragments and Derivatives | |
| H-Ser-Val-Thr-Glu-Gln-Gly-Ala-Glu-Leu-Ser-Asn-Glu-Glu-NH₂ | 4 |
| H-DSer-Val-AlloThr-Glu-Gln-Gly-Ala-Glu-Nle-Ser-Asn-NMeGlu-GluOMe-NH₂ | 5 |
| H-Val-Thr-Glu-Gln-Gly-Ala-Glu-Leu-Ser-Asn-Glu-Glu-Arg-NH₂ | 6 |
| H-Nva-AlloThr-Glu-Gln-Gly-Ala-Glu-Nle-Ser-Asn-NMeGlu-Glu-Orn-NH₂ | 7 |
| Central 12 Residue Fragments and Derivatives | |
| H-Val-Thr-Glu-Gln-Gly-Ala-Glu-Leu-Ser-Asn-Glu-Glu-NH₂ | 8 |
| H-Nva-AlloThr-Glu-Gln-Gly-Ala-Glu-Nle-Ser-Asn-NMeGlu-GluOMe-NH₂ | 9 |
| H-Chex-Thr-NMeGlu-Gln-Gly-Ala-Glu-Leu-Hyp-DAsn-Glu-DGln-NH₂ | 10 |
| 11 Residue Fragments and Derivatives | |
| H-Val-Thr-Glu-Gln-Gly-Ala-Glu-Leu-Ser-Asn-Glu-NH₂ | 11 |
| H-Nva-AlloThr-Glu-Gln-Gly-Ala-Glu-Nle-Ser-Asn-NMeGlu-NH₂ | 12 |
| H-Thr-Glu-Gln-Gly-Ala-Glu-Leu-Ser-Asn-Glu-Glu-NH₂ | 13 |
| H-AlloThr-Glu-Gln-Gly-Ala-Glu-Nle-Ser-Asn-NMeGlu-GluOMe-NH₂ | 14 |
| Central 10 Residue Fragments and Derivatives | |
| H-Thr-Glu-Gln-Gly-Ala-Glu-Leu-Ser-Asn-Glu-NH₂ | 15 |
| H-AlloThr-Glu-Gln-Nva-Ala-Glu-Nle-Ser-Asn-NMeGlu-NH₂ | 16 |
| H-DSer-Glu-Gln-Gly-Ala-Glu-Leu-DSer-DAsn-DGln-NH₂ | 17 |
| 9 Residue Fragments and Derivatives | |
| H-Ser-Val-Thr-Glu-Gln-Gly-Ala-Glu-Leu-NH₂ | 18 |
| H-DSer-Val-Thr-Glu-Gln-Nva-Ala-Glu-Nle-NH₂ | 19 |
| H-Hyp-Val-Thr-Glu-Gln-Gly-βAla-Glu-Aha-NH₂ | 20 |
| H-Val-Thr-Glu-Gln-Gly-Ala-Glu-Leu-Ser-NH₂ | 21 |
| H-Nva-Thr-Glu-Gln-Nva-Ala-Glu-Leu-DSer-NH₂ | 22 |
| H-Chex-Thr-Glu-Gln-Gly-βAla-Glu-Leu-Hyp-NH₂ | 23 |
| H-Thr-Glu-Gln-Gly-Ala-Glu-Leu-Ser-Asn-NH₂ | 24 |
| H-AlloThr-Glu-Gln-Nva-Ala-Glu-Leu-Ser-DAsn-NH₂ | 25 |
| H-DSer-Glu-Gln-Gly-βAla-Glu-Leu-Ser-DGln-NH₂ | 26 |
| H-Glu-Gln-Gly-Ala-Glu-Leu-Ser-Asn-Glu-NH₂ | 27 |
| H-NMeGlu-Gln-Gly-Ala-Glu-Nle-Ser-Asn-NMeGlu-NH₂ | 28 |
| H-IsoGln-Gln-Gly-βAla-Glu-Leu-Ser-Asn-GluOMe-NH₂ | 29 |
| H-Gln-Gly-Ala-Glu-Leu-Ser-Asn-Glu-Glu-NH₂ | 30 |
| H-DAsn-Gly-Ala-Glu-Nle-Ser-Asn-Glu-NMeGlu-NH₂ | 31 |
| H-IsoGln-Gly-βAla-Glu-Leu-Ser-Asn-Glu-GluOMe-NH₂ | 32 |
| H-Gly-Ala-Glu-Leu-Ser-Asn-Glu-Glu-Arg-NH₂ | 33 |
| H-Nva-Ala-Glu-Nle-Ser-Asn-Glu-Glu-Orn-NH₂ | 34 |
| H-βAla-Ala-Glu-Leu-DSer-Asn-Glu-Glu-NMeArg-NH₂ | 35 |

A peptide inhibitor of trans-endothelial migration can be secreted in response to adiponectin during inflammation. The peptide can be proteolytically derived from a 14.3.3 zeta delta (14.3.3.0) protein. B cells can tonically inhibit T cell trafficking by secretion of the peptide inhibitor of trans-endothelial migration peptide. Cadherin-15 is bound to the surface of endothelial cells by the peptide, promoting the synthesis and release of sphingosine-1-phosphate, which in turn impedes trafficking of T cells while not impacting recruitment of other leukocytes. With age, both expression of adiponectin receptors on B cells and secretion of the peptide inhibitor of trans-endothelial migration peptide in response to adiponectin diminishes, suggesting immune senescence of the pathway. Similar changes have been seen in persons with type-1 diabetes, rheumatoid arthritis. However, following administration of exogenous peptide inhibitor of trans-endothelial migration peptide, T cell trafficking is re-established. Similar results were also seen in animal models of peritonitis, hepatic ischemia=reperfusion injury, and *Salmonella* infection. (Chimen, M. et al. 2015 Nat. Med. 21(5):467-475)

U.S. Pat. No. 8,815,795 pertains to adiponectin, a 247-amino acid sequence suggested for the prevention or treatment of eye diseases. It is proposed that adiponectin can decrease inflammatory cytokines and has efficacy for prevention or therapeutic benefit for diseases of the eye such as dry eye (syndrome), eye complications from the use of contact lenses, alleviating ocular surface irregularities, decreasing inflammatory cytokines, and increasing conjunctival goblet cell density as well as providing a composition for eye cleaners or lubricants for contact lenses wearer. There is no mention that the disclosed 14-mer peptide, a small sequence secreted by B-cells in response to adiponectin, has any value, nor that it can decrease inflammatory cytokines. U.S. Pat. No. 9,073,965 presents a short adiponectin peptide mimetic of the disclosed SEQ ID NO:1 and pharmaceutical preparations/compositions comprising it in relation to the treatment of cancer and atherosclerosis. US20150051137 also discloses SEQ ID NO:1, but relates the peptide or analogues thereof for treatment and/or prophylaxis of chronic inflammatory disease and autoimmune diseases such as diabetes mellitus (type 1), rheumatoid arthritis, Crohn's disease, nephropathy, atherosclerosis, psoriasis, liver diseases and uveitis. However, none of the prior art discloses the use of the disclosed peptide, derivatives or analogues thereof for treating dry eye and ocular surface diseases of inflammation.

Rainer et al. (WO2013104928) have proposed that because adiponectin is a pleiotropic agent, having roles in metabolic homeostasis as well as potentially activating B lymphocyte secretion of a peptide inhibiting migration of T cells, therapeutic agents targeting pathways downstream of; adiponectin, involved in regulation of T cell migration, could target specific modes of action.

The use of the disclosed SEQ ID NO:1, a peptide, variants, analogues, derivatives, modified peptides and pharmaceutically acceptable salts thereof, has been proposed by the inventors to be effective as an anti-inflammatory peptide for the treatment of dry eye disease. In a mouse model a Tear Film break-up time assay was conducted to determine the time for dry spots to appear on the corneal surface of the eye after blinking. This assay provides a method to evaluate the tear film stability as well as determining if evaporative dry eye is present. Tears comprise three layers: an innermost layer of hydrophilic mucin, a slimy substance produced by the goblet cells that coats the ocular surface epithelium; an aqueous tear layer produced by the lacrimal glands which floats on the mucin layer and is approximately 0.9% saline; and a superficial thin lipid layer produced by the Meibomian glands, which helps with uniform tear spreading and to slow down tear evaporation. This three-layer structure stabilizes the tear film and enables the tear film to keep the eye moist, create a smooth surface for light to pass through the eye, nourish the front of the eye, and provide protection from injury and infection. Factors that disturb the delicate homeostatic balance of the ocular surface system can adversely affect tear film stability and osmolarity, resulting in osmotic, mechanical, and inflammatory damage.

FIG. 1 illustrates a murine study of tear film break-up with a longer time indicating a more stable tear film. Subjects with normal tear quantity but an unstable tear film can explain dry eye symptoms. Tear instability can indicate an imbalance in tear composition causing tears to evaporate too fast or improper adhesion to the eye surface. Alternatively, insufficient lipid secretion by the Meibomian glands due to Meibomian gland dysfunction can also cause tear film instability. Evaluations were done at five and 10 days with around >3-5 seconds a normal time. <2.2-3.0 seconds marginal and <2.2 seconds low and a high likelihood of dry eye symptoms.

The results of the tear film break-up indicate that both 5% Lifitegrast and 0.1% peptide inhibitor of trans-endothelial migration peptide can ameliorate induced dry eye in a mouse model. The group dosed with 0.1% peptide had noticeably improved tear film times at both intervals. Details of the Tear Film Break-up experiment are presented in Example 1.

Figure 2:
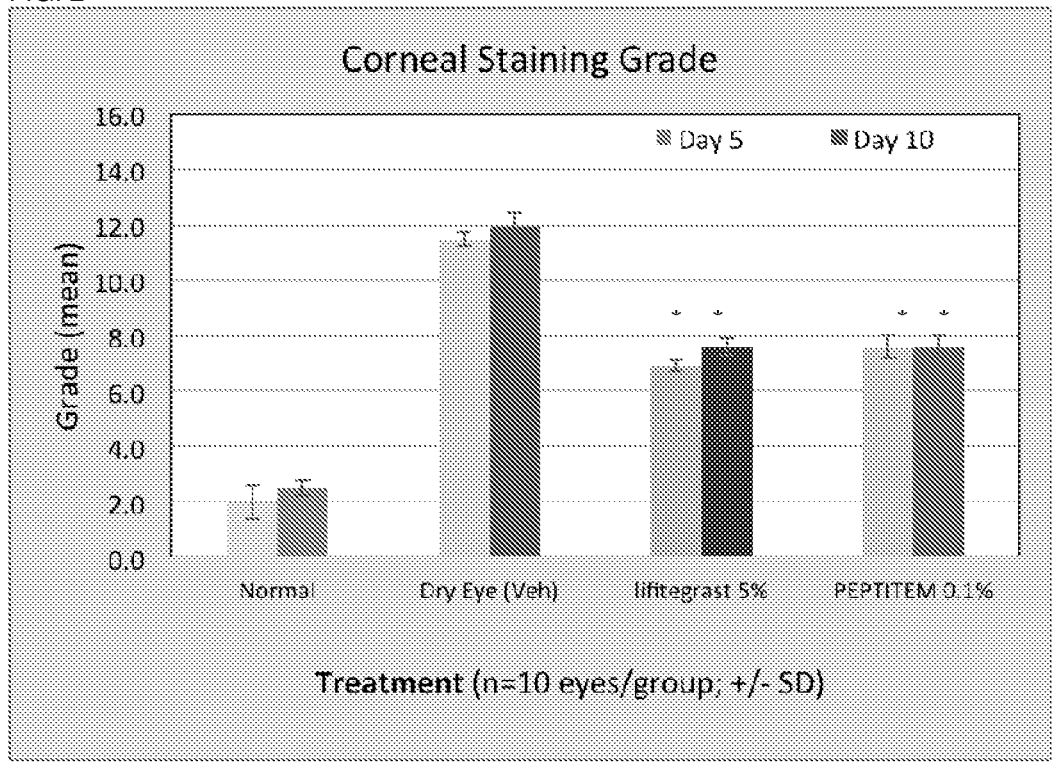
FIG. 2 is a bar chart illustrating changes in corneal staining when dry eye is treated with either 5% Lifitegrast or 0.1% SEQ ID NO:1, a peptide inhibitor of trans-endothelial migration (PEPITEM) at five and ten days post treatment.
Figure 3:
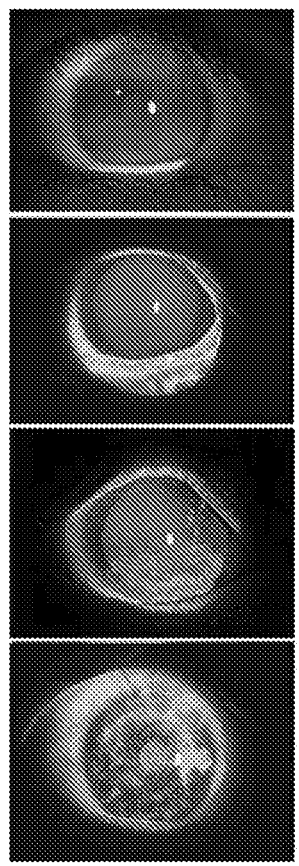
FIG. 3 depicts four photos of corneal surface staining.
Figure 3:
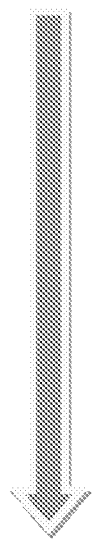

Example 2 is a corneal staining assay to determine damage to the murine dry eye subject's cornea epithelia. FIG. 2 illustrates grading of the staining results. The fluorescein staining detects disruptions, changes in the contour and injury of the epithelium of the cornea. The lower the staining grade the less serious the corneal damage. Again, as in the tear film break-up study, FIG. 2 illustrates that both 5% Lifitegrast and 0.1% SEQ ID NO:1 improved corneal disruptions. FIG. 3 provides cobalt-blue light observations of corneal surface stains where disruptions are identified by green staining, representing at the lower grade damage to the corneal epithelium while at the higher grade, severe injury resulting from a variety of causes including for example, areas of opacity, misuse of contact lenses, corneal inflammations, scratches and objects within the cornea.

T-cells are recruited from the blood into extra-vascular tissues during acute inflammation. However, in chronic inflammatory diseases, including but not limited to atherosclerosis, rheumatoid arthritis, Crohn's disease, etc., an inappropriate accumulation of T-cells in the diseased tissue contributes to pathogenesis. Mechanisms by which T-cell trafficking is regulated during inflammation are not well understood, making the development of therapies difficult. While not wishing to be bound by any theory, when control of the regulatory pathway for trafficking T cell is out of control, T cells can be permitted access to inflamed tissues, causing constant inflammation, resulting in a chronic disease state. Peptide inhibitor of trans-endothelial migration peptide therapies could offer new pathways for regulating the inflammatory response.

The conjunctiva is the surface lining the interior surface of the eyelid and covers the white of the eye, the sclera. Non-keratinized, stratified squamous epithelium with goblet cells as well as stratified columnar epithelium makes up the conjunctiva. Because the conjunctiva is richly vascularized and has numerous microvessels, it is ideally suited for imagining studies. FIGS. 4A-4D represent scatter-plots of the change in the number of activated T cells within the eye's conjunctiva. Example 3 presents the assay to measure the change in activated T cells in the murine dry eye model. A normal range for activated T cells is between 15% and 22%. After 10 days only 0.1% peptide inhibitor of trans-endothelial migration peptide re-established activated T cells within the normal range 21.67% with the control at 18.86%.

Other potential therapies for dry eye include Lifitegrast (trade name XLIDRA) and Restasis® Ophthalmic Emulsion (cyclosporine) eye drops. Lifitegrast treats keratoconjunctivitis sicca (dry eye syndrome) by down-regulating a mechanism in which T cells mediate inflammation. Lifitegrast acts by inhibiting the integrin, lymphocyte function-associated antigen 1 (LFA-1), from binding to intercellular adhesion molecule 1 (ICAM-1).

Cyclosporin (ciclosporin, cyclosporine) acts to decrease the activity of T cells and their immune response. When cyclosporin binds to cyclophilin, a multifunctional protein that facilitates protein folding, it can act as a protein chaperone, and regulates the activity of other proteins. The phosphatase activity of calcineurin is inhibited by the cyclosporin/cyclophilin complex, which in turn blocks the activation of transcription factors that up-regulate the expression of inflammatory cytokines by T lymphocytes.

The use of peptide inhibitor of trans-endothelial migration peptide(s) in combination with other pharmaceuticals, including but not limited to, Lifitegrast, Restasis eye drops and the like are also contemplated.

Methods

The following Methods were used to evaluate the efficacy, anti-inflammatory activity and the therapeutic potential of a peptide inhibitor of trans-endothelial migration peptide compared with 5% Lifitegrast in a mouse model of desiccating stress-induced dry eye (experimental dry eye; EDE).

A. Test System with Induced Experimental Dry Eye:

Desiccating stress was induced in six to eight-week-old female C57BL/6 mice by subcutaneous injection of 0.5 mg/0.2 mL scopolamine hydrobromide (Sigma-Aldrich, St. Louis, Mo.) three times a day (3×0.3 ml given at 4.5 hr. intervals) with exposure to an air draft and 30% ambient humidity), which was maintained throughout the dosing period. During these experiments, the animals' behavior, food, and water intake were not restricted. Treatment was terminated and testing was conducted at endpoints of either five or ten days.

B. Treatment Groups:

Each treatment group comprised 5 animals (n=10 eyes/group) randomly assigned. The groups were treated topically as follows:
1. Untreated (Normal) control mice that were not exposed to desiccating stress or treated topically
2. EDE mice treated with balanced salt solution (BSS, vehicle, Alcon, Fort Worth, Tex.)
3. EDE mice treated with 5% (wt) Lifitegrast (Shire Plc)
4. EDE mice treated with 0.01% peptide inhibitor of trans-endothelial migration peptide, (SEQ ID NO:1, CS Bio, Menlo Park, Calif.)

C. Dosing Procedure:

All treatment groups received 2 μL eye drops three times a day. The mice in each treatment group: EDE treated with BSS, EDE treated with 5% Lifitegrast, and EDE treated with 0.1% SEQ ID NO:1 were dosed/treated three times/day with 2 uL eye drops of each treatment, respectively (except Normal group). Additionally all groups (except Normal) were also dosed three times/day with the scopolamine solution.

D. Tear Film Break-Up Time (TBUT):

TBUT was determined by dropping 1 μL of 1% sodium fluorescein into the inferior conjunctival sac using a micropipette. After three blinks, tear film break-up time (BUT) was recorded in seconds using slit lamp biomicroscopy (BQ-900; Haag-Streit, Bern, Switzerland) under cobalt blue light. Results are illustrated in FIG. 1.

E. Corneal Fluorescein Staining:

Ninety seconds after the fluorescein drops were added to measure TBUT, punctate staining on the corneal surface was evaluated in a masked fashion. Each cornea was divided into four quadrants that were scored individually. Corneal fluorescein staining severity score was calculated using a 4-point scale: 0=absent; 1=slightly punctate staining <30 spots; 2=punctate staining >30 spots, but not diffuse; 3=severe diffuse staining but no positive plaque; and 4=positive fluorescein plaque. The four scores were added to generate a final grade (possible total of 16 points). Results are presented in FIGS. 2 and 3.

F. Flow Cytometry:

Flow cytometry was performed for quantitation of CD4+ and CCR5+ T cells from the conjunctiva as previously described (Yoon K C, Heo H, Kang I S, et al. Cornea (2008) 27: 454-460). The tissues were teased and shaken at 37□C. for 60 minutes with 0.5 mg/mL collagenase type D.

After grinding with a syringe plunger and passage through a cell strainer, cells were obtained, centrifuged, and resuspended in PBS with 1% bovine serum albumin. After washing, the samples were incubated with fluorescein-conjugated anti-CD4 antibody (BD Biosciences, San Jose, Calif.), phycoerythrin-conjugated anti-CCR5 antibody (BD Biosciences), and isotype control antibody at 37□C. for 30 minutes.

The number of CD4+ and CCR5+ T cells was counted by a FACSCalibur cytometer with CellQuest software (BD Biosciences). Results for each treatment group are presented in FIGS. 4A-4D.

Statistical Analysis:

Statistical differences in the tear break-up time, corneal staining and normal score results were evaluated by one-way ANOVA, with post hoc analysis. Kruskal-Wallis and Mann-Whitney test was used to compare flow cytometry between groups. A P value <0.05 was considered statistically significant.

The following Examples present experimental results conducted in murine subjects to evaluate the peptide inhibitor of trans-endothelial migration peptide's activity, efficacy and the therapeutic potential.

Example 1

Tear Film Break-up: This experiment evaluated the anti-inflammatory activity and efficacy of the peptide inhibitor of trans-endothelial migration peptide in ameliorating Desiccation-induced Dry Eye (DED). Eyes were evaluated for time for dry spots to appear on the corneal surface of the eye after blinking. This assay provides a method to evaluate the tear film stability as well as determining if an evaporative dry eye is present. The longer the time before tear film break-up indicates a more stable tear film. Subjects with normal tear quantity but an unstable tear film can explain dry eye symptoms. Tear instability can indicate an imbalance in tear composition causing tears to evaporate too fast or improper adhesion to the eye surface. Alternatively, insufficient lipid secretion by the Meibomian glands due to Meibomian gland dysfunction can also cause tear film instability. Evaluations were done at five and 10-day endpoints with around >3-5 seconds a normal time. <2.2-3.0 seconds marginal and <2.2 seconds low and a high likelihood of dry eye symptoms and no discernable improvement in efficacy.

FIG. 1 illustrates results in a murine study of tear film break-up. Both 5% Lifitegrast and 0.1% peptide inhibitor of trans-endothelial migration peptide (SEQ ID NO:1) can ameliorate DED in a mouse model. The group dosed with 0.1% SEQ ID NO:1 had noticeably improved tear film times at both endpoints compared to untreated (Dry Eye, Veh) and 5% Lifitegrast.

Example 2

Corneal Staining:

The purpose of the corneal staining assay was to evaluate damage to the cornea epithelia in the murine DED subject either as a consequence of inducing dry eye or due to peptide inhibitor of trans-endothelial migration peptide. Additionally, a peptide inhibitor of trans-endothelial migration peptide was evaluated for anti-inflammatory activity and efficacy in a mouse model of DED. Fluorescein staining detects disruptions, detectable injury to the epithelium surface cells of the cornea and changes in the contour of the cornea. The lower the staining grade the less severe the corneal damage. Corneal staining was assessed in four quadrants using a 4-point scale with 16 being the maximum score. FIG. 2 illustrates grading of the staining results. Again, as in the tear film break-up study, both 5% Lifitegrast and 0.1% peptide inhibitor of trans-endothelial migration peptide, SEQ ID NO:1, improved corneal disruptions resulting from the induced dry eye as each had a lower grade than the untreated dry eyes. FIG. 3 provides photos of cobalt-blue light observations of corneal surface stains where disruptions are identified by green staining, and blue indicates non-staining, non-injured areas of the cornea. The results at the top represent an example of lower graded damage (Grade 1) to the corneal epithelium while at the higher grades (bottom photo), illustrates severe injury resulting from a variety of causes including for example, areas of opacity, misuse of contact lenses, corneal inflammations, scratches and objects within the cornea can be causative in severe, Grade 4, staining.

Example 3

Figure 4A:
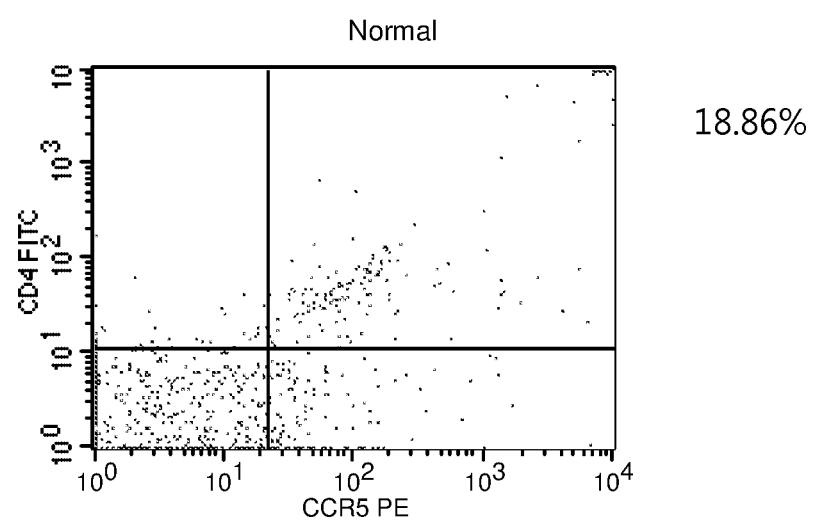
Figure 4B:
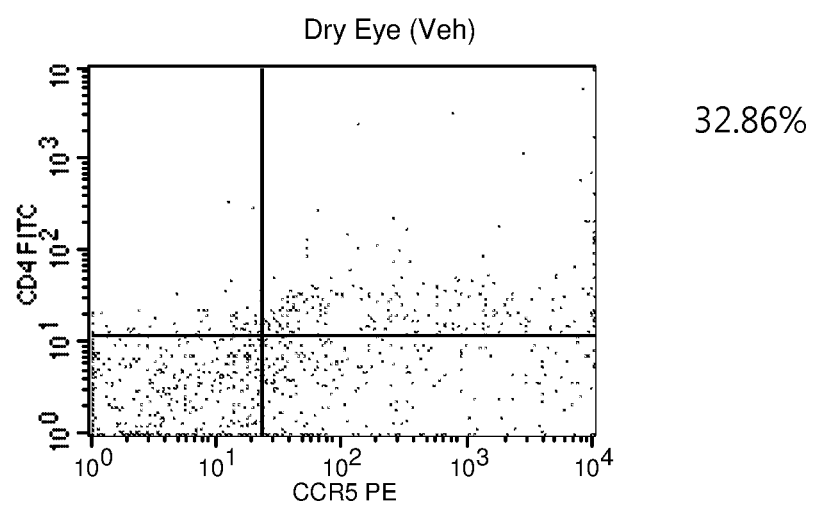
Figure 4C:
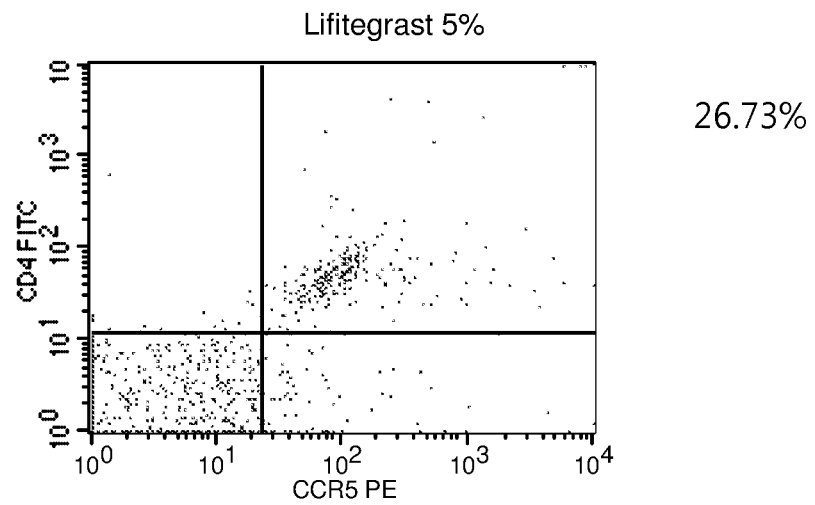
Figure 4D:
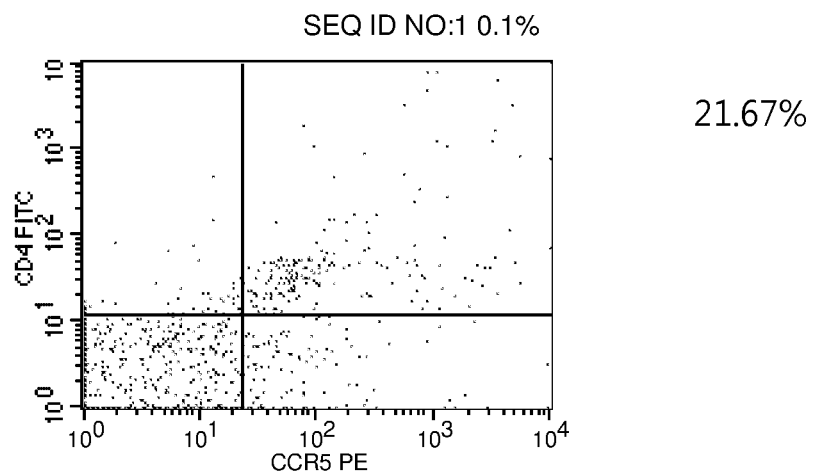

Change in Activated T Cells:

Eye conjunctiva was evaluated for the number of Activated T cells present in the conjunctiva for each group in the murine Dry Eye study. This assay provides a method to evaluate the infiltration and presence of Activated T Cells as a consequence of inflammation of the conjunctiva due to DED. Each red dot represents an Activated T Cell. The greater the percentage of Activated T Cells, the greater the inflammation within the conjunctiva as Activated T Cells have traversed the epithelia cells. In mice a normal range of Activated T Cells can be from 15% to around 22%. Values greater than 22% suggest moderate to >30% as severe inflammation. Subjects with excessively inflamed conjunctiva, seen as a very red surface, with or without an unstable tear film can explain the high number of Activated T Cells present. Because the conjunctiva, as the surface lining the interior surface of the eyelid and covering the white of the eye, the sclera and comprising both non-keratinized, stratified squamous epithelium with goblet cells as well as stratified columnar epithelium, the potential for infiltration of activated T cells as a consequence of inflammation is highly probable. FIG. 4A-4D represent scatter plots of the change in the number of Activated T Cells within each subject's eye conjunctiva at 10 days. FIG. 4A represents a Normal eye, FIG. 4B represents an untreated Dry Eye, FIG. 4C represents an induced Dry Eye treated with 5% Lifitegrast and FIG. 4D represents an induced Dry Eye treated with 0.1% SEQ ID NO:1. The results indicate that after 10 days only 0.1% SEQ ID NO:1 re-established Activated T Cell levels within the normal range as the percentage was 21.67% with the control at 18.86%.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence. The disclosures of all publications, patents, patent applications and published patent applications referred to herein by an identifying citation are hereby incorporated herein by reference in their entirety. Websites references using "World-Wide-Web" at the beginning of the Uniform Resource Locator (URL) can be accessed by replacing "World-Wide-Web" with "www."

What is claimed is:

1. A composition comprising one or more peptides comprising the peptides selected from the group consisting of H-DSer-Val-AlloThr-Glu-Gln-Gly-Ala-Glu-Nle-Ser-Asn-NMeGlu-Glu-Orn-NH$_2$ (SEQ ID NO:2), H-Hyp-Val-Thr-NMeGlu-Gln-Gly-Ala-Glu-Leu-Hyp-DAsn-Glu-Glu-Aha-NH$_2$(SEQ ID NO:3), H-Ser-Val-Thr-Glu-Gln-Gly-Ala-Glu-Leu-Ser-Asn-Glu-Glu-NH$_2$ (SEQ ID NO:4), H-DSer-Val-AlloThr-Glu-Gln-Gly-Ala-Glu-Nle-Ser-Asn-NMeGlu-GluOMe-NH$_2$(SEQ ID NO:5), H-Val-Thr-Glu-Gln-Gly-Ala-Glu-Leu-Ser-Asn-Glu-Glu-Arg-NH$_2$ (SEQ ID NO:6), H-Nva-AlloThr-Glu-Gln-Gly-Ala-Glu-Nle-Ser-Asn-NMe-Glu-Glu-Orn-NH$_2$(SEQ ID NO:7), H-Val-Thr-Glu-Gln-Gly-Ala-Glu-Leu-Ser-Asn-Glu-Glu-NH2 (SEQ ID NO:8), H-Nva-AlloThr-Glu-Gln-Gly-Ala-Glu-Nle-Ser-Asn-NMe-Glu-GluOMe-NH$_2$ (SEQ ID NO:9), H-Chex-Thr-NMeGlu-Gln-Gly-Ala-Glu-Leu-Hyp-DAsn-Glu-DGln-NH$_2$(SEQ ID NO:10), H-Val-Thr-Glu-Gln-Gly-Ala-Glu-Leu-Ser-Asn-Glu-NH$_2$ (SEQ ID NO:11), H-Nva-AlloThr-Glu-Gln-Gly-Ala-Glu-Nle-Ser-Asn-NMeGlu-NH$_2$ (SEQ ID NO:12), H-Thr-Glu-Gln-Gly-Ala-Glu-Leu-Ser-Asn-Glu-Glu-NH$_2$ (SEQ ID NO:13), H-AlloThr-Glu-Gln-Gly-Ala-Glu-Nle-Ser-Asn-NMeGlu-GluOMe-NH$_2$ (SEQ ID NO:14), H-Thr-Glu-Gln-Gly-Ala-Glu-Leu-Ser-Asn-Glu-NH2 (SEQ ID NO:15), H-AlloThr-Glu-Gln-Nva-Ala-Glu-Nle-Ser-Asn-NMeGlu-NH2 (SEQ ID NO:16), H-DSer-Glu-Gln-Gly-Ala-Glu-Leu-DSer-DAsn-DGln-NH$_2$(SEQ ID NO:17), H-Ser-Val-Thr-Glu-Gln-Gly-Ala-Glu-Leu-NH$_2$ (SEQ ID NO:18), H-DSer-Val-Thr-Glu-Gln-Nva-Ala-Glu-Nle-NH$_2$ (SEQ ID NO:19), H-Hyp-Val-Thr-Glu-Gln-Gly-βAla-Glu-Aha-NH$_2$(SEQ ID NO:20), H-Val-Thr-Glu-Gln-Gly-Ala-Glu-Leu-Ser-NH$_2$ (SEQ ID NO:21), H-Nva-Thr-Glu-Gln-Nva-Ala-Glu-Leu-DSer-NH$_2$ (SEQ ID NO:22), H-Chex-Thr-Glu-Gln-Gly-βAla-Glu-Leu-Hyp-NH$_2$(SEQ ID NO:23), H-Thr-Glu-Gln-Gly-Ala-Glu-Leu-Ser-Asn-NH$_2$ (SEQ ID NO:24), H-AlloThr-Glu-Gln-Nva-Ala-Glu-Leu-Ser-DAsn-NH$_2$ (SEQ ID NO:25), H-DSer-Glu-Gln-Gly-βAla-Glu-Leu-Ser-DGln-NH$_2$(SEQ ID NO:26), H-Glu-Gln-Gly-Ala-Glu-Leu-Ser-Asn-Glu-NH$_2$ (SEQ ID NO:27), H-NMeGlu-Gln-Gly-Ala-Glu-Nle-Ser-Asn-NMeGlu-NH$_2$ (SEQ ID NO:28), H-IsoGln-Gln-Gly-βAla-Glu-Leu-Ser-Asn-GluOMe-NH$_2$(SEQ ID NO:29), H-Gln-Gly-Ala-Glu-Leu-Ser-Asn-Glu-Glu-NH$_2$ (SEQ ID NO:30), H-DAsn-Gly-Ala-Glu-Nle-Ser-Asn-Glu-NMeGlu-NH$_2$ (SEQ ID NO:31), H-IsoGln-Gly-βAla-Glu-Leu-Ser-Asn-Glu-GluOMe-NH$_2$(SEQ ID NO:32), H-Gly-Ala-Glu-Leu-Ser-Asn-Glu-Glu-Arg-NH$_2$ (SEQ ID NO:33), H-Nva-Ala-Glu-Nle-Ser-Asn-Glu-Glu-Orn-NH$_2$ (SEQ ID NO:34), and H-βAla-Ala-Glu-Leu-DSer-Asn-Glu-Glu-NMeArg-NH$_2$(SEQ ID NO:35).

2. A composition of one or more peptides consisting of a peptide selected from the group consisting of H-DSer-Val-AlloThr-Glu-Gln-Gly-Ala-Glu-Nle-Ser-Asn-NMeGlu-Glu-Orn-NH$_2$ (SEQ ID NO:2), H-Hyp-Val-Thr-NMeGlu-Gln-Gly-Ala-Glu-Leu-Hyp-DAsn-Glu-Glu-Aha-NH$_2$(SEQ ID NO:3), H-Ser-Val-Thr-Glu-Gln-Gly-Ala-Glu-Leu-Ser-Asn-Glu-Glu-NH$_2$ (SEQ ID NO:4), H-DSer-Val-AlloThr-Glu-Gln-Gly-Ala-Glu-Nle-Ser-Asn-NMeGlu-GluOMe-NH$_2$ (SEQ ID NO:5), H-Val-Thr-Glu-Gln-Gly-Ala-Glu-Leu-Ser-Asn-Glu-Glu-Arg-NH$_2$ (SEQ ID NO:6), H-Nva-AlloThr-Glu-Gln-Gly-Ala-Glu-Nle-Ser-Asn-NMeGlu-Glu-Orn-NH$_2$ (SEQ ID NO:7), H-Val-Thr-Glu-Gln-Gly-Ala-Glu-Leu-Ser-Asn-Glu-Glu-NH$_2$ (SEQ ID NO:8), H-Nva-AlloThr-Glu-Gln-Gly-Ala-Glu-Nle-Ser-Asn-NMeGlu-GluOMe-NH$_2$ (SEQ ID NO:9), H-Chex-Thr-NMeGlu-Gln-Gly-Ala-Glu-Leu-Hyp-DAsn-Glu-DGln-NH$_2$(SEQ ID NO:10), H-Val-Thr-Glu-Gln-Gly-Ala-Glu-Leu-Ser-Asn-Glu-NH$_2$ (SEQ ID NO:11), H-Nva-AlloThr-Glu-Gln-Gly-Ala-Glu-Nle-Ser-Asn-NMeGlu-NH$_2$ (SEQ ID NO:12), H-Thr-Glu-Gln-Gly-Ala-Glu-Leu-Ser-Asn-Glu-Glu-NH$_2$ (SEQ ID NO:13), H-AlloThr-Glu-Gln-Gly-Ala-Glu-Nle-Ser-Asn-NMeGlu-GluOMe-NH$_2$ (SEQ ID NO:14), H-Thr-Glu-Gln-Gly-Ala-Glu-Leu-Ser-Asn-Glu-NH$_2$ (SEQ ID NO:15), H-AlloThr-Glu-Gln-Nva-Ala-Glu-Nle-Ser-Asn-NMeGlu-NH$_2$ (SEQ ID NO:16), H-DSer-Glu-Gln-Gly-Ala-Glu-Leu-DSer-DAsn-DGln-NH$_2$(SEQ ID NO:17), H-Ser-Val-Thr-Glu-Gln-Gly-Ala-Glu-Leu-NH$_2$ (SEQ ID NO:18), H-DSer-Val-Thr-Glu-Gln-Nva-Ala-Glu-Nle-NH$_2$ (SEQ ID NO:19), H-Hyp-Val-Thr-Glu-Gln-Gly-βAla-Glu-Aha-NH$_2$(SEQ ID NO:20), H-Val-Thr-Glu-Gln-Gly-Ala-Glu-Leu-Ser-NH$_2$ (SEQ ID NO:21), H-Nva-Thr-Glu-Gln-Nva-Ala-Glu-Leu-DSer-NH$_2$ (SEQ ID NO:22), H-Chex-Thr-Glu-Gln-Gly-βAla-Glu-Leu-Hyp-NH$_2$(SEQ ID NO:23), H-Thr-Glu-Gln-Gly-Ala-Glu-Leu-Ser-Asn-NH$_2$ (SEQ ID NO:24), H-AlloThr-Glu-Gln-Nva-Ala-Glu-Leu-Ser-DAsn-NH$_2$ (SEQ ID NO:25), H-DSer-Glu-Gln-Gly-βAla-Glu-Leu-Ser-DGln-NH$_2$(SEQ ID NO:26), H-Glu-Gln-Gly-Ala-Glu-Leu-Ser-Asn-Glu-NH$_2$ (SEQ ID NO:27), H-NMeGlu-Gln-Gly-Ala-Glu-Nle-Ser-Asn-NMeGlu-NH$_2$ (SEQ ID NO:28), H-IsoGln-Gln-Gly-βAla-Glu-Leu-Ser-Asn-GluOMe-NH$_2$(SEQ ID NO:29), H-Gln-Gly-Ala-Glu-Leu-Ser-Asn-Glu-Glu-NH$_2$ (SEQ ID NO:30), H-DAsn-Gly-Ala-Glu-Nle-Ser-Asn-Glu-NMeGlu-NH$_2$ (SEQ ID NO:31), H-IsoGln-Gly-βAla-Glu-Leu-Ser-Asn-Glu-GluOMe-NH$_2$(SEQ ID NO:32), H-Gly-Ala-Glu-Leu-Ser-Asn-Glu-Glu-Arg-NH$_2$ (SEQ ID NO:33), H-Nva-Ala-Glu-Nle-Ser-Asn-Glu-Glu-Orn-NH$_2$ (SEQ ID NO:34), and H-βAla-Ala-Glu-Leu-DSer-Asn-Glu-Glu-NMeArg-NH$_2$(SEQ ID NO:35).

3. A pharmaceutical composition comprising the composition of claim 1, and a pharmaceutically acceptable excipient.

4. The pharmaceutical composition of claim 3 wherein the peptide is present in an amount sufficient to improve tear film stability in the dry eye when the pharmaceutical composition is administered to the subject in need thereof.

5. The pharmaceutical composition of claim 3 wherein the pharmaceutically acceptable excipient comprises at least one of a solvent, a buffering agent, a preservative, a chelating agent, an antioxidant, a stabilizer, an emulsifying agent, a suspending agent, and a diluent.

6. The composition of claim 1 wherein the peptide is a synthetic peptide.

7. The pharmaceutical composition of claim 3, further comprising 1.0% to 10.0% Lifitegrast or a salt thereof.

8. The pharmaceutical composition of claim 4, wherein the administration is selected from the group consisting of topical treatment, intravitreal injection, subconjunctival injection, intramuscular injection, subcutaneous injection, intravenous injection, intracameral injection, and implantation into the subject's eye.

9. The pharmaceutical composition of claim 4, wherein the dry eye presents at least one symptom or clinical sign of dry eye selected from the group consisting of a change in tear secretion, a change in tear clearance, ocular surface damage, corneal epithelial defects, a change in ocular surface cells, a change in tear film stability, a change in tear volume, a change in tear film composition, a change in tear osmolarity, and any combination thereof.

10. The pharmaceutical composition of claim 4, wherein the dry eye presents at least one symptom or clinical sign of dry eye selected from the group consisting of hypolacrimation, tear deficiency, xerophthalmia, Sjogren's syndrome dry eye, non-Sjogren's syndrome dry eye, keratoconjunctivitis sicca, aqueous tear-deficiency dry eye (ADDE), evaporative dry eye (EDE), environmental dry eye, Stevens-Johnson syndrome, ocular pemphigoid blepharitis marginal, eyelid-closure failure, sensory nerve paralysis, allergic conjunctivitis-associated dry eye, post-viral conjunctivitis dry eye, post-cataract surgery dry eye, VDT operation-associated dry eye, and contact lens wearing-associated dry eye.

11. The pharmaceutical composition of claim 4, wherein the dry eye is an ocular disease associated with inflammation selected from the group consisting of uveitis, scleritis, post-eye surgery inflammation, corneal transplantation, corneal wound healing, conjunctivitis, retinal disease, glaucoma, ocular hypertension, pterygium and a combination thereof.

12. The pharmaceutical composition of claim 4, wherein the peptide is present in an amount between about 0.01% (wt) to about 5.0% (wt) of the final composition.

13. The pharmaceutical composition of claim 4, wherein the composition is in a formulation selected from the group consisting of a solution, suspension, syrup, liquid, gel, hydrogel, emulsion, liposome, aerosol, mist, film, suspension, plug, polymer, implant, contact lens, ocular insert, nanoparticle, microparticle, a sustained release formulation, and a formulation suitable for an ocular medical device.

* * * * *